US 8,164,251 B2

(12) United States Patent
Funahashi et al.

(10) Patent No.: US 8,164,251 B2
(45) Date of Patent: Apr. 24, 2012

(54) AROMATIC AMINE DERIVATIVES AND ORGANIC ELECTROLUMINESCENCE DEVICES USING THE SAME

(75) Inventors: Masakazu Funahashi, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1417 days.

(21) Appl. No.: 11/561,164

(22) Filed: Nov. 17, 2006

(65) Prior Publication Data

US 2009/0085468 A1 Apr. 2, 2009

(30) Foreign Application Priority Data

Nov. 18, 2005 (JP) ................. 2005-334154

(51) Int. Cl.
*H01J 1/63* (2006.01)
(52) U.S. Cl. ........ 313/504; 428/690; 428/917; 313/506; 564/426; 564/427; 564/428; 546/264; 556/413; 548/440
(58) Field of Classification Search .......... 428/690, 428/917; 313/504, 506; 564/426, 428, 427; 546/264; 556/413; 548/440
See application file for complete search history.

(56) References Cited

U.S. PATENT DOCUMENTS

| | | | | |
|---|---|---|---|---|
| 5,935,721 | A * | 8/1999 | Shi et al. ................ | 428/690 |
| 6,022,895 | A | 2/2000 | Zimmer et al. | |
| 7,651,786 | B2 * | 1/2010 | Matsuura et al. ........... | 428/690 |
| 2005/0064233 | A1 * | 3/2005 | Matsuura et al. ........... | 428/690 |
| 2005/0277645 | A1 * | 12/2005 | Moree et al. ............. | 514/252.1 |
| 2007/0009760 | A1 | 1/2007 | Inoue et al. | |
| 2007/0018569 | A1 | 1/2007 | Kawamura et al. | |
| 2008/0125609 | A1 | 5/2008 | Vestweber et al. | |

FOREIGN PATENT DOCUMENTS

| | | |
|---|---|---|
| AU | 9858408 | 2/1999 |
| BR | 9801346 | 12/2000 |
| CA | 2231975 | 9/1998 |
| CN | 1197059 | 10/1998 |
| CN | 1852910 A | 10/2006 |
| CN | 1871192 | 11/2006 |
| DE | 198 05 370 A1 | 9/1998 |
| EP | 0 864 559 | 9/1998 |
| EP | 1 623 970 | 2/2006 |
| EP | 1 659 129 A1 | 5/2006 |
| EP | 1 707 550 A1 | 10/2006 |
| HK | 1015351 | 12/2002 |
| HU | 9800555 | 6/1999 |
| IL | 123647 | 1/2004 |
| JP | 2-306248 | 12/1990 |
| JP | 9-323957 | 12/1997 |
| JP | 10-338665 | 12/1998 |
| JP | 11-154594 | 6/1999 |
| JP | 2004-339064 | 12/2004 |
| JP | 2004-339134 | 12/2004 |
| JP | 2005-8559 | 1/2005 |
| JP | 2005-44791 | 2/2005 |
| JP | 2005-85599 | 3/2005 |
| NO | 9801121 | 9/1998 |
| WO | WO 2004/101491 A1 | 11/2004 |
| WO | WO 2005/033118 A1 | 4/2005 |
| WO | WO 2005/054162 | 6/2005 |
| WO | WO 2005/097093 | 10/2005 |
| WO | 2006058737 | 6/2006 |
| ZA | 9802157 | 11/1998 |

OTHER PUBLICATIONS

Chemical Abstracts, vol. 97 abs. No. AN 1982:38646 Caplus, Entered May 12, 1984, pp. 27-28.

* cited by examiner

*Primary Examiner* — Gregory Listvoyb
(74) *Attorney, Agent, or Firm* — Oblon, Spivak, McClelland, Maier & Neustadt, L.L.P.

(57) ABSTRACT

An aromatic amine derivative with a specified structure. An organic electroluminescence device which comprises one or more organic thin film layers having at least one light emitting layer sandwiched between a cathode and an anode, wherein at least one of the organic thin film layers comprises the aromatic amine derivative singly or in combination. The organic EL device employing the aromatic amine derivative has sufficient lifetime, exhibits an enhanced efficiency of light emission, and emits highly pure blue light.

20 Claims, 2 Drawing Sheets

AROMATIC AMINE DERIVATIVES AND ORGANIC ELECTROLUMINESCENCE DEVICES USING THE SAME

TECHNICAL FIELD

The present invention relates to an organic electroluminescence ("electroluminescence" will be occasionally referred to as "EL", hereinafter) device. More particularly, it relates to an organic EL device with an enhanced efficiency of light emission and emits highly pure blue light and an aromatic amine derivative realizing the device.

BACKGROUND ART

Organic EL devices which utilize organic substances are expected to be useful for application as an inexpensive full color display device of the solid light emission type having a great size and various developments on the organic EL devices are. being conducted. In general an organic EL device has a construction comprising a light emitting layer and a pair of electrodes sandwiching the light emitting layer. The light emission of the organic EL device is a phenomenon in which, when an electric field is applied between the two electrodes, electrons are injected from the cathode side and holes are injected from the anode side, the electrons are recombined with the holes in the light emitting layer to form an excited state, and energy generated when the excited state returns to the ground state is emitted as light.

As compared with an inorganic light emitting diode, conventional organic EL devices require high driving voltage and only exhibited low luminance or low efficiency of light emission. Moreover, characteristic degradation of the conventional organic EL devices was also extravagant and as a result, they were not practically used. Although recent organic EL devices are improved step by steps, it has been still demanded to develop organic EL devices with an enhanced efficiency of light emission and with a prolonged lifetime.

For example, there is disclosed such a technique using a single monoanthracene compound as an organic light emitting material (refer to Patent Literature 1 below). However, in this technique, a luminance obtained by using the material is as low as 1650 $cd/m^2$, for example, at a current density of 165 $mA/cm^2$, and an efficiency of light emission thereof is very low, i.e., only 1 cd/A, which is practically unusable. Also, there is disclosed a technique using a single bisanthracene compound as an organic light emitting material (refer to Patent Literature 2 below). However, in this technique, a current efficiency of light emission obtained by using the material is also as low as around 1 to 3 cd/A. Therefore, further improvement of the technique has been demanded for rendering it practically usable. On the other hand, there is disclosed a technique using a distyryl compound adding styrylamine or so in an organic light emitting material in order for realizing an organic EL device with a prolonged lifetime refer to Patent Literature 3 below). However, the device described therein fails to show a sufficiently long lifetime and, therefore, further improvement has been demanded.

Furthermore, a technique of employing mono- or bis-anthracene compound and a distyryl compound as an organic light emitting medium layer is disclosed (refer to Patent Literature 4 below). However in these technologies, a conjugated structure of the styryl compound shifted a light emission spectrum in the long-wave direction and deteriorated the purity of color.

Still further, Patent Literature 5 below discloses a blue luminescence device with a of stilbene derivatives. However, despite the superiority in an efficiency of light emission, because the devices are not sufficient in its purity of color, further improvement for a purpose of full color displays application was required.

Patent Literature 1: Japanese Unexamined Patent Application

Laid-Open No. Hei 11-3782

Patent Literature 2: Japanese Unexamined Patent Application

Laid-Open No. Hei 8-12600

Patent Literature 3: International Application Published under

PCT No. WO 94/006157

Patent Literature 4: Japanese Unexamined Patent Application

Laid-Open No. 2001-284050

Patent Literature 5: International Application Published under

PCT No. WO 02/020459

DISCLOSURE OF THE INVENTION

The present invention has been made to overcome the above problems and has an object of providing an organic EL device which emits blue light with high purity of color having an enhanced efficiency of light emission and with a long lifetime; and an object of providing an aromatic amine derivative realizing the EL device.

As a result of extensive researches for developing aromatic amine derivatives having the above suitable properties and organic EL devices using the aromatic amine derivatives, the inventors have found that the object of the present invention can be achieved by using aromatic amine derivatives represented by a following general formula (I) that has a skeleton such as tetrahydrochrysene, dihydronaphthalene, indene, indenoindene and so on in its molecule. Such being the case, the present invention has been accomplished on the basis of the foregoing findings and information.

Namely, the present invention provides an aromatic amine derivative represented by a following general formula (I):

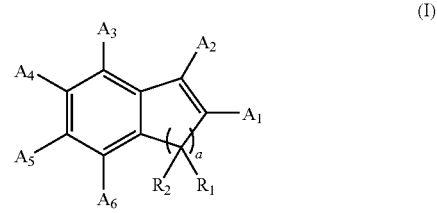

In the general formula (I), $A_1$ to $A_6$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms or a substituted or unsubstituted heterocyclic group having 5 to 50 ring carbon atoms;

a couple of $A_1$ and $A_2$, a couple of $A_2$ and $A_3$, a couple of $A_3$ and $A_4$, a couple of $A_4$ and $A_5$, and a couple of $A_5$ and $A_6$ may bond each other to form a saturated or unsaturated ring;

$R_1$ and $R_2$ each independently represents a hydrogen atom, a substituted or unsubstituted alkyl group having 1 to 20 carbon atoms, a substituted or unsubstituted aryl group having 5 to 20 ring carbon atoms, a substituted or unsubstituted aralkyl group having 6 to 20 ring carbon atoms, a substituted or unsubstituted cycloalkyl group having 3 to 20 ring carbon atoms or a substituted or unsubstituted silyl group having 1 to 20 carbon atoms;

a represents an integer of 1 to 3; when a is 2 or greater, $R_1$ and $R_2$ may be the same with or different from each other; while at least one among $A_1$ to $A_5$ represents a following general formula (II) or a general formula (III):

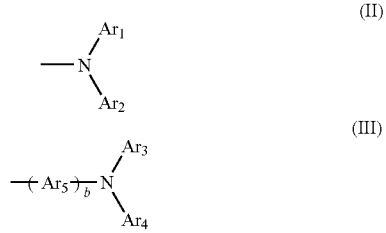

wherein $Ar_1$ to $Ar_4$ each independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms or a substituted or unsubstituted heterocyclic group having 5 to 50 ring carbon atoms; when $Ar_1$ to $Ar_4$ are aryl groups, a couple of $Ar_1$ and $Ar_2$, and a couple of $Ar_3$ and $Ar_4$ may bond each other to form a saturated or unsaturated ring;

$Ar_5$ is any one of bivalent groups made by removing one hydrogen atom from each group of $Ar_1$ to $Ar_4$; and b represents an integer of 1 to 3; when b is 2 or greater, plural $Ar_{5s}$ may be the same with or different from each other.

Further, the present invention provides an organic EL device which comprises one or more organic thin film layers having at least one light emitting layer sandwiched between a cathode and an anode, wherein at least one of the organic thin film layers comprises the aromatic amine derivative singly or as its mixture component.

The organic EL device employing the aromatic amine derivative of the present invention reveals practically sufficient luminance even under low applied voltage, exhibits an enhanced efficiency of light emission, and is resistant to degrade even after a long time usage demonstrating a prolonged lifetime.

PREFERRED EMBODIMENT TO CARRY OUT THE INVENTION

Figure 1:
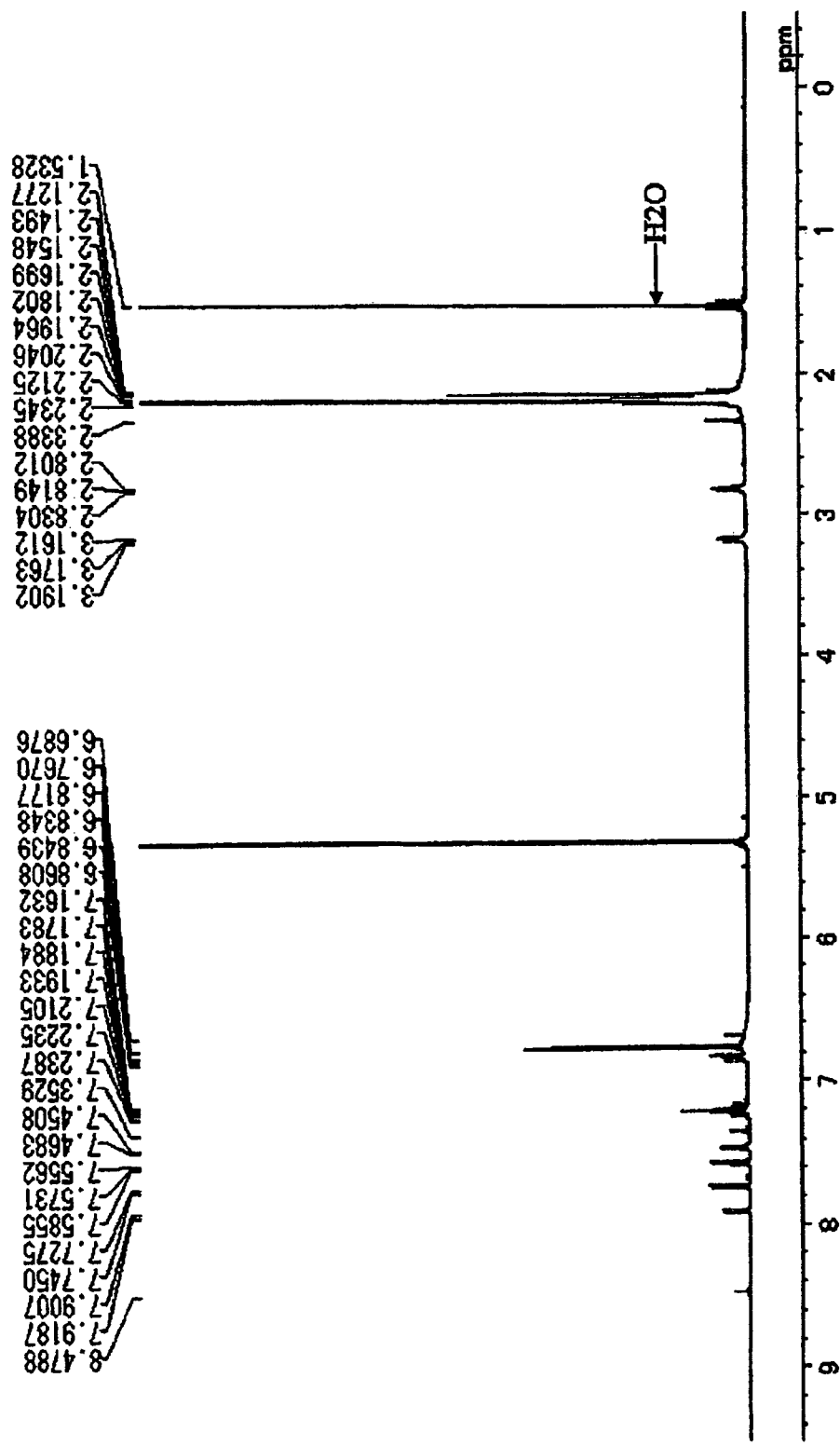
FIG. 1 is a chart showing $^1$H-Nuclear Magnetic Resonance (NMR) spectrum of the Compound D-3-1 being the aromatic amine derivative of the present invention obtained in Synthesis Example 1.

The present invention provides an aromatic amine derivative represented by a following general formula (I):

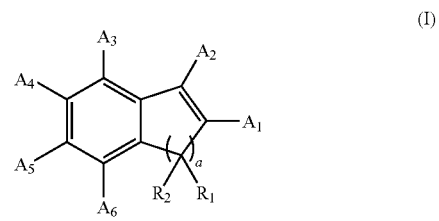

The aromatic amine derivative represented by the general formula (I) will be explained below.

In the general formula (I), $A_1$ to $A_6$ each independently represents a hydrogen atom, a substituted or unsubstituted alkyl group having 1 to 50 (preferably 1 to 20) carbon atoms, a substituted or unsubstituted aryl group having 5 to 50 (preferably 5 to 20) ring carbon atoms, a substituted or unsubstituted aralkyl group having 6 to 50 (preferably 6 to 20) ring carbon atoms, a substituted or unsubstituted cycloalkyl group having 3 to 50 (preferably 5 to 12) ring carbon atoms, a substituted or unsubstituted alkoxyl group having 1 to 50 (preferably 1 to 6) carbon atoms, a substituted or unsubstituted aryloxy group having 5 to 50 (preferably 5 to 18) ring carbon atoms, a substituted or unsubstituted arylamino group having 5 to 50 (preferably 5 to 18) ring carbon atoms, a substituted or unsubstituted alkylamino group having 1 to 20 (preferably 1 to 6) carbon atoms, a substituted or unsubstituted silyl group having 1 to 20 (preferably 1 to 10) carbon atoms or a substituted or unsubstituted heterocyclic group having 5 to 50 (preferably 5 to 20) ring carbon atoms;

$R_1$ and $R_2$ each independently represents a hydrogen atom, a substituted or unsubstituted alkyl group having 1 to 20 (preferably 1 to 20) carbon atoms, a substituted or unsubstituted aryl group having 6 to 20 (preferably 5 to 20) ring carbon atoms, a substituted or unsubstituted aralkyl group having 6 to 20 (preferably 6 to 20) ring carbon atoms, a substituted or unsubstituted cycloalkyl group having 3 to 20 (preferably 5 to 12) ring carbon atoms or a substituted or unsubstituted silyl group having 1 to 20 (preferably 1 to 10) carbon atoms; however, at least one among $A_1$ to $A_6$ represents a following general formula (II) or a general formula (III):

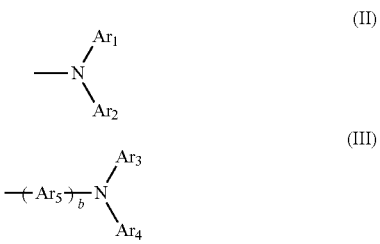

In the general formulae (II) and (III), $Ar_1$ to $Ar_4$ each independently represents a substituted or unsubstituted alkyl group having 1 to 50 (preferably 1 to 20) carbon atoms, a substituted or unsubstituted aryl group having 5 to 50 (preferably 5 to 20) ring carbon atoms, a substituted or unsubstituted aralkyl group having 6 to 50 (preferably 6 to 20) ring carbon atoms, a substituted or unsubstituted cycloalkyl group having 3 to 50 (preferably 5 to 12) ring carbon atoms or a substituted or unsubstituted heterocyclic group having 5 to 50 (preferably 5 to 20) ring carbon atoms; when $Ar_1$ to $Ar_4$ are aryl groups, a couple of $Ar_1$ and $Ar_2$, and a couple of $Ar_3$ and $Ar_4$ may bond each other to form a saturated or unsaturated ring; and $Ar_5$ is any one of bivalent groups made by removing one hydrogen atom from each group of $Ar_1$ to $Ar_4$.

Examples of the alkyl group represented by $A_1$ to $A_6$, $R_1$, $R_2$ and $Ar_1$ to $Ar_4$ include methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group, α-benzyloxybenzyl group, etc.

Examples of the aryl group represented by $A_1$ to $A_6$, $R_1$, $R_2$ and $Ar_1$ to $Ar_4$ include phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group, naphthyl group, 5-methylnaphthyl group, anthryl group, pyrenyl group, chrycenyl group, fluoranthenyl group, perilenyl group, etc.

Examples of the substituted or unsubstituted aralkyl group represented by $A_1$ to $A_6$, $R_1$, $R_2$ and $Ar_1$ to $Ar_4$ include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, 1-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group, etc.

Examples of the cycloalkyl group represented by $A_1$ to $A_6$, $R_1$, $R_2$ and $Ar_1$ to $Ar_4$ include cyclopropyl group, cyclobutyl group, cyclopentyl group, cyclohexyl group, cycloheptyl group, cyclooctyl group, cyclononyl group, bicycloheptyl group, bicyclooctyl group, tricycloheptyl group, adamanthyl group, etc. Among those, cyclopentyl group, cyclohexyl group, cycloheptyl group, bicycloheptyl group, bicyclooctyl group, and adamanthyl group are preferable.

Examples of the alkoxy group represented by $A_1$ to $A_6$ include methoxy group, ethoxy group, propoxy group, isopropoxy group, butoxy group, isobutoxy group, sec-butoxy group, tert-butoxy group, various kinds of pentyloxy groups, various kinds of hexyloxy groups, etc.

Examples of the aryloxy group represented by $A_1$ to $A_6$ include phenoxy group, tolyloxy group, naphthyloxy group, etc.

Examples of the arylamino group represented by $A_1$ to $A_6$ include diphenylamino group, ditolylamino group, dinaphthylamino group, naphthylphenylamino group, etc.

Examples of the alkylamino group represented by $A_1$ to $A_6$ include dimethylamino group, diethylamino group, dihexylamino group, etc.

Specific examples of the silyl group represented by $A_1$ to $A_6$, $R_1$ and $R_2$ include trimethylsilyl group, triethylsilyl group, t-butyldimethylsilyl group, vinyldimethylsilyl group, propyldimethylsilyl group, triphenylsilyl group, etc.

Examples of the heterocyclic group represented by $A_1$ to $A_6$ and $Ar_1$ to $Ar_4$ include moieties of imidazole, benzimidazole, pyrrole, furan, thiophene, benzothiophene, oxadiazoline, indoline, carbazole, pyridine, quinoline, isoquinoline, benzoquinone, pyrazoline, imidazolidine, piperidine, etc.

In the general formula (I), a represents an integer of 1 to 3; when a is 2 or greater, $R_1$ and $R_2$ may be the same with or different from each other.

In the general formula (I), a couple of $A_1$ and $A_2$, a couple of $A_2$ and $A_3$, a couple of $A_3$ and $A_4$, a couple of $A_4$ and $A_5$ and a couple of $A_5$ and $A_6$ may bond each other to form a saturated or unsaturated ring. Further, when $Ar_1$ to $Ar_4$ are aryl groups in the general formulae (II) and (III), a couple of $Ar_1$ and $Ar_2$, and a couple of $Ar_3$ and $Ar_4$ may bond each other to form a saturated or unsaturated ring.

Examples of the ring include a cycloalkane having 4 to 12 carbon atoms such as cyclobutane, cyclopentane, cyclohexane, adamantane, norbornane, etc.; a cycloalkene having 4 to 12 carbon atoms such as cyclobutene, cyclopentene, cyclohexene, cycloheptene, cyclooctene, etc.; a cycloalkadiene having 6 to 12 carbon atoms such as cyclohexadiene, cycloheptadiene, cyclooctadiene, etc.; an aromatic ring having 6 to 50 carbon atoms such as benzene, naphthalene, phenanthrene, anthracene, pyrene, chrysene, acenaphthylene, etc.; and a heterocyclic group having 5 to 50 carbon atoms such as imidazole, pyrrole, furan, thiophene, pyridine, carbazole, azepin, etc.

In the general formulae (II) and (III), b represents an integer of 1 to 3; when b is 2 or greater, plural $Ar_5$s may be the same with or different from each other.

Examples of the substituent for $A_1$ to $A_6$, $R_1$, $R_2$ and $Ar_1$ to $Ar_5$ include a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 60 ring carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, an amino group, a halogen atom, a cyano group, a nitro group, a hydroxyl group, a carboxyl group, etc.

Among those, the alkyl group having 1 to 10 carbon atoms, a cycloalkyl group having 5 to 7 ring carbon atoms and the alkoxy group having 1 to 10 carbon atoms are preferable, the alkyl group having 1 to 6 carbon atoms and the cycloalkyl group having 5 to 7 ring carbon atoms are more preferable; further, methyl group, ethyl group, n-propyl group, isopropyl group, n-butyl group, s-butyl group, t-butyl group, n-pentyl group, n-hexyl group, cyclopentyl group and cyclohexyl group are particularly preferable.

In the aromatic amine derivative represented by the general formula (I) of the present invention, it is preferable that at least one among $A_3$ to $A_6$ has a structure expressed by the foregoing general formula (II) or by the foregoing general formula (III).

Further, it is preferable that the aromatic amine derivative represented by the general formula (I) of the present invention has a structure represented by a following general formula (IV).

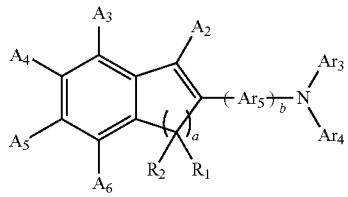

(IV)

In the general formula (IV), $A_2$ to $A_6$ are the same as those defined in the general formula (I); a couple of $A_3$ and $A_4$, a couple of $A_4$ and $A_5$, and a couple of $A_5$ and $A_6$ may bond each other to form a saturated or unsaturated ring; $R_1$ and $R_2$ are the same as those defined in the general formula (I); a represents an integer of 1 to 3; when a is 2 or greater, $R_1$ and $R_2$ may be the same with or different from each other; $Ar_3$ and $Ar_4$ are the same as those defined in the foregoing general formula (III); $Ar_5$ is the same as that defined in the foregoing general formula (III);

b represents an integer of 0 to 3; when b is 2 or greater, plural $Ar_5$s may be the same with or different from each other, It is preferable that the aromatic amine derivative represented by the general formula (I) of the present invention has a structure with $Ar_3$ and $Ar_4$ in the general formula (IV) each independently represents either a substituted or unsubstituted aryl group having 5 to 50 ring carbon atoms or a substituted or unsubstituted heterocyclic group having 5 to 60 ring carbon atoms; $Ar_5$ is a bivalent group made by removing one hydrogen atom from each group of $Ar_3$ and $Ar_4$, and at least one among $A_3$ to $A_6$ has a structure of the foregoing general formula (II) or the foregoing general formula (III).

It is preferable that the aromatic amine derivative represented by the general formula (I) of the present invention has a structure represented by a following general formula (V):

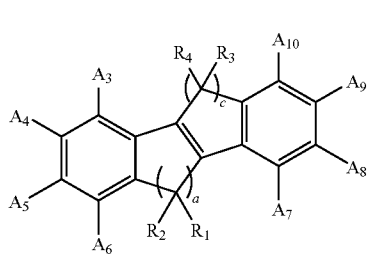

(V)

In the general formula (V), $A_3$ to $A_{10}$ are the same as $A_1$ to $A_6$ defined in the general formula (I); a couple of $A_3$ and $A_4$, a couple of $A_4$ and $A_5$, a couple of $A_5$ and $A_6$, a couple of $A_7$ and $A_8$, a couple of $A_8$ and $A_9$, and a couple of $A_9$ and $A_{10}$ may bond to each other to form a saturated or unsaturated ring; $R_1$ to $R_4$ are the same as $R_1$ and $R_2$ defined above about the general formula (I); a and c each independently represents an integer of 1 to 3 respectively; when a and/or c is 2 or greater, plural of $R_1$ and $R_2$ and/or plural of $R_3$ and $R_4$ may be the same with or different from each other; however, at least one among $A_3$ to $A_6$ and at least one among $A_7$ to $A_{10}$ each independently represents the above general formula (II) or the above general formula (III).

It is preferable that the aromatic amine derivative represented by the general formula (I) of the present invention has a structure represented by a following general formula (VI).

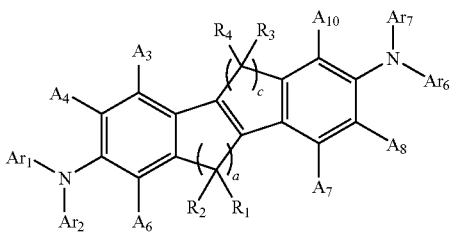

(VI)

In the general formula (VI), $A_3$ to $A_{10}$ are the same as $A_1$ to $A_6$ defined in the general formula (I); a couple of $A_3$ and $A_4$, and a couple of $A_7$ and $A_8$ may bond each other to form a saturated or unsaturated ring structure; $R_1$ to $R_4$ are the same as $R_1$ and $R_2$ defined above about the general formula (I); a and c each independently represents an integer of 1 to 3 respectively; when a and/or c is 2 or greater, plural of $R_1$ and $R_2$ and/or plural of $R_3$ and $R_4$ may be the same with or different from each other; and $Ar_1$ to $Ar_7$ are the same as those defined about $Ar_1$ to $Ar_4$ in the general formulae (II) and (III).

It is preferable that the aromatic amine derivative of the present invention has a structure represented by a following general formula (VII):

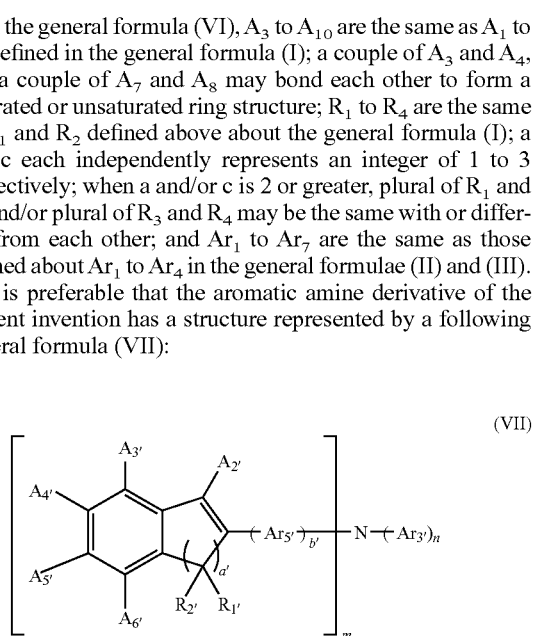

(VII)

In the general formula (VII), $A_{2'}$ to $A_{6'}$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms or a substituted or unsubstituted heterocyclic group having 5 to 50 ring carbon atoms; a couple of $A_{3'}$ and $A_{4'}$, a couple of $A_{4'}$ and $A_{5'}$, and a couple of $A_{5'}$ and $A_{6'}$ may bond each other to form a saturated or unsaturated ring; $R_{1'}$ and $R_{2'}$ each independently represents a hydrogen atom, a substituted or unsubstituted alkyl group having 1 to 20 carbon atoms, a substituted or unsubstituted aryl group having 5 to 20 ring carbon atoms, a substituted or unsubstituted aralkyl group having 6 to 20 ring carbon atoms, a substituted or unsubstituted cycloalkyl group having 3 to 20 ring carbon atoms or a substituted or unsubstituted silyl group having 1 to 20 carbon atoms; a' represents an integer of 1 to 3; when a' is 2 or greater, plural of $R_{1'}$ and $R_{2'}$ may be the same with or different from each other; $Ar_{3'}$ independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms or a substituted or unsubstituted heterocyclic group having 5 to 50 ring carbon atoms; $Ar_{5'}$ is any one of bivalent groups made by removing one hydrogen atom from each group of $Ar_{3'}$; b' represents an integer of 1 to 3; when b' is 2 or greater, plural $Ar_{5'}$s may be the same with or different from each other; m represents an integer of 2 or 3, n represents an integer of 0 or 1, and m+n equal 3; further, plural of $A_{2'}$ to $A_{6'}$, $R_{1''}$, $R_{2'}$ or $Ar_{5'}$ may be the same with, or different from each other.

Specific examples, substituent and preferable range about the number of carbon atoms regarding with $A_7$ to $A_{10}$, $R_5$, $R_4$ and $Ar_6$ to $Ar_8$ in the general formulae (IV) to (VII) are the same as explained about the foregoing general formula (I).

Specific examples of the aromatic amine derivative represented by the general formula (I) of the present invention include the following compounds, though not limited thereto.

D-1-1

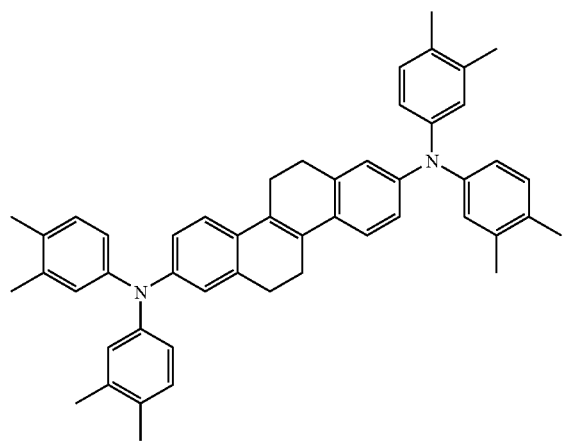

D-1-2

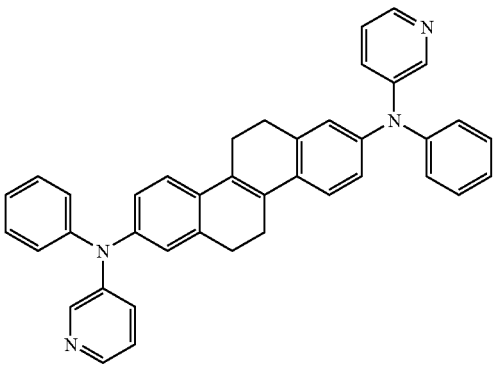

D-1-3

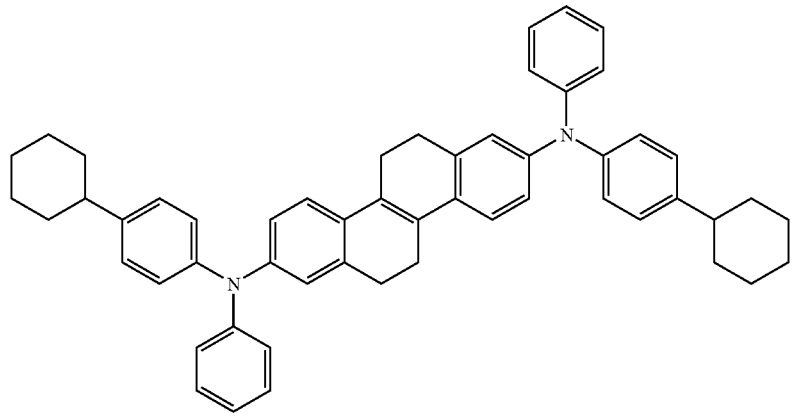

D-1-4

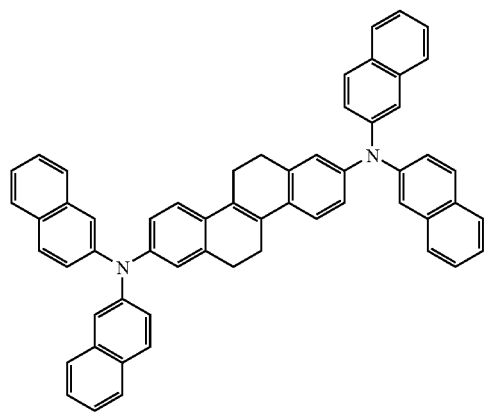

D-1-5

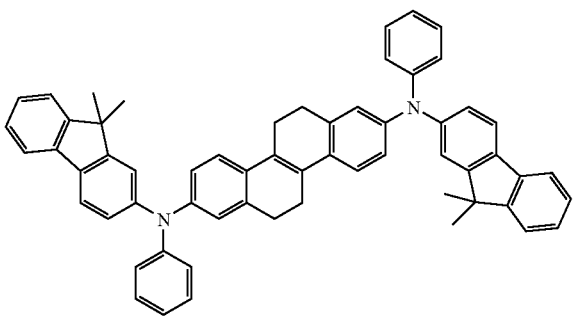

-continued
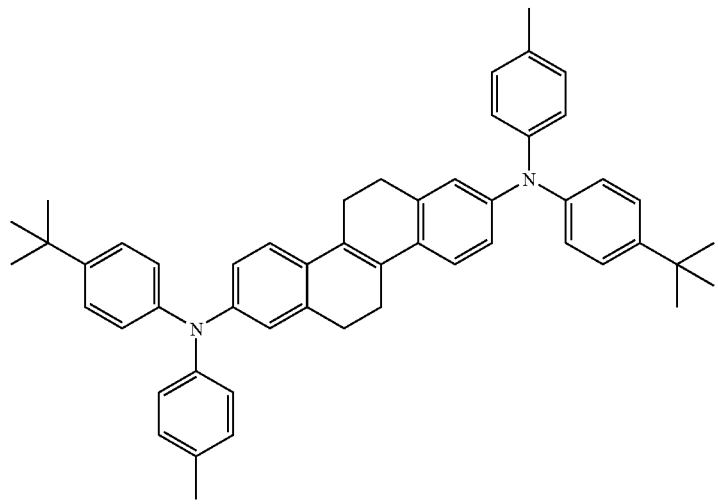
D-1-6
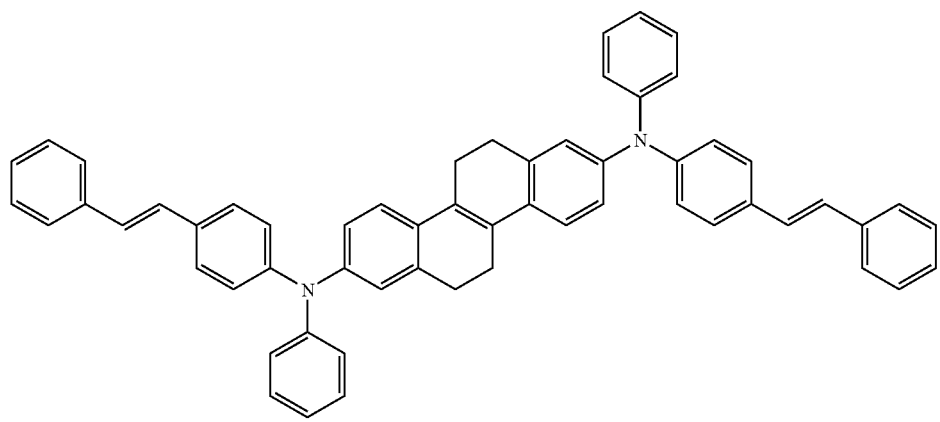
D-1-7
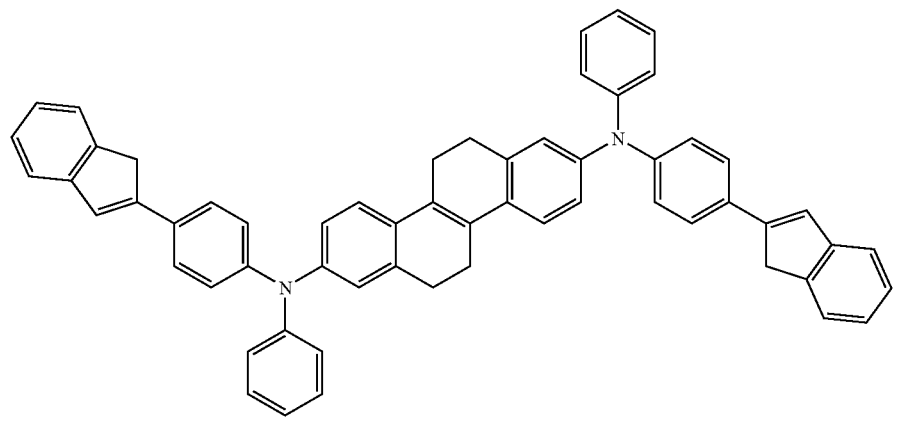
D-1-8

-continued
D-2-1
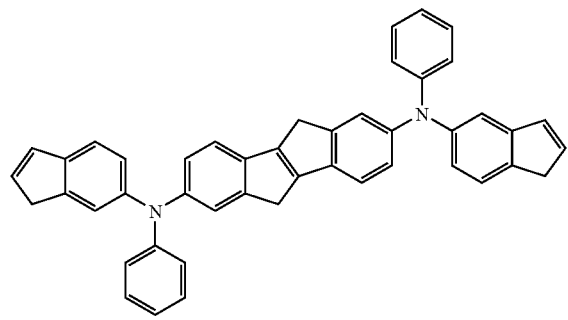
D-2-2
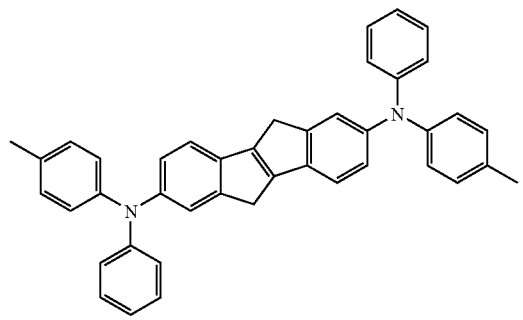
D-2-3
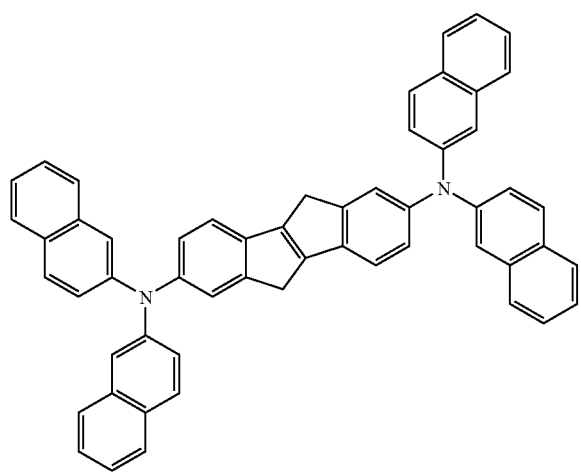
D-2-4
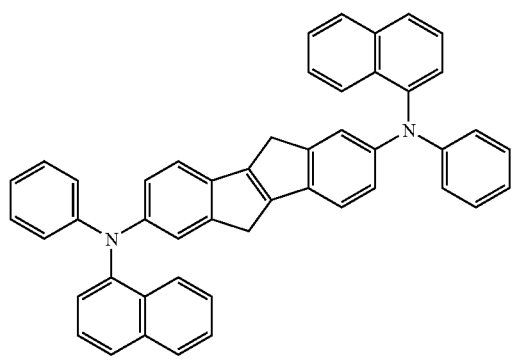
D-2-5
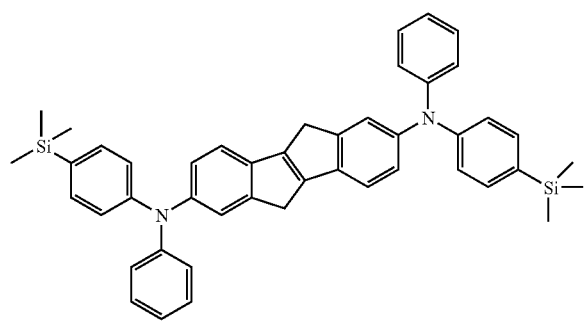
D-2-6
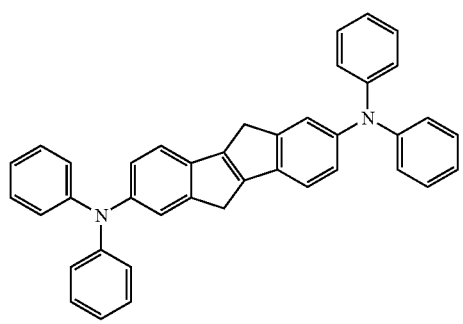
D-2-7
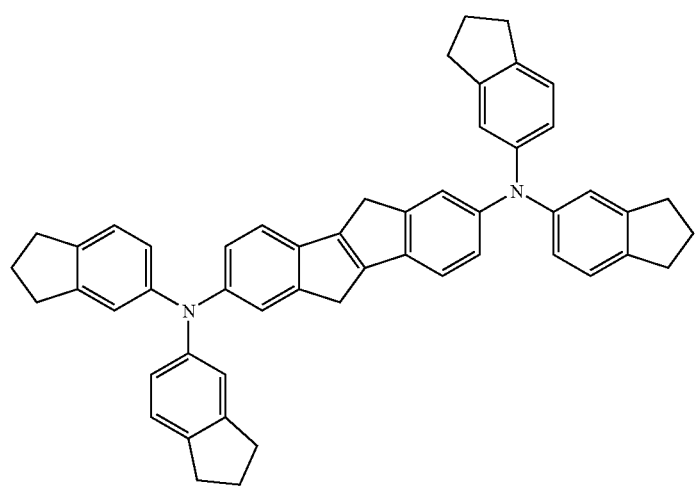

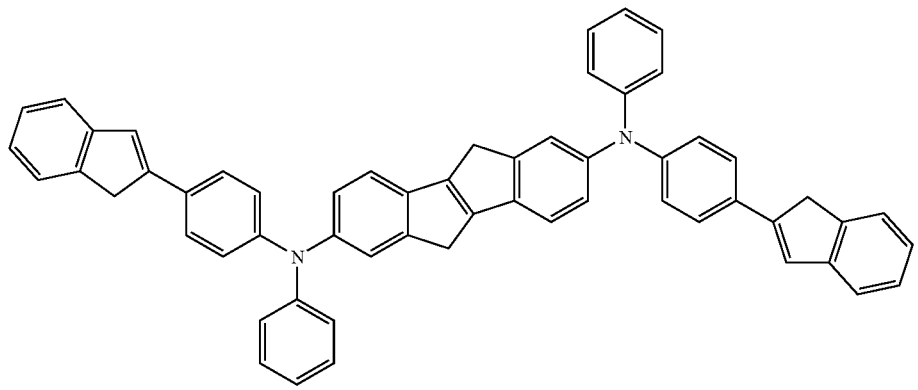
D-2-8
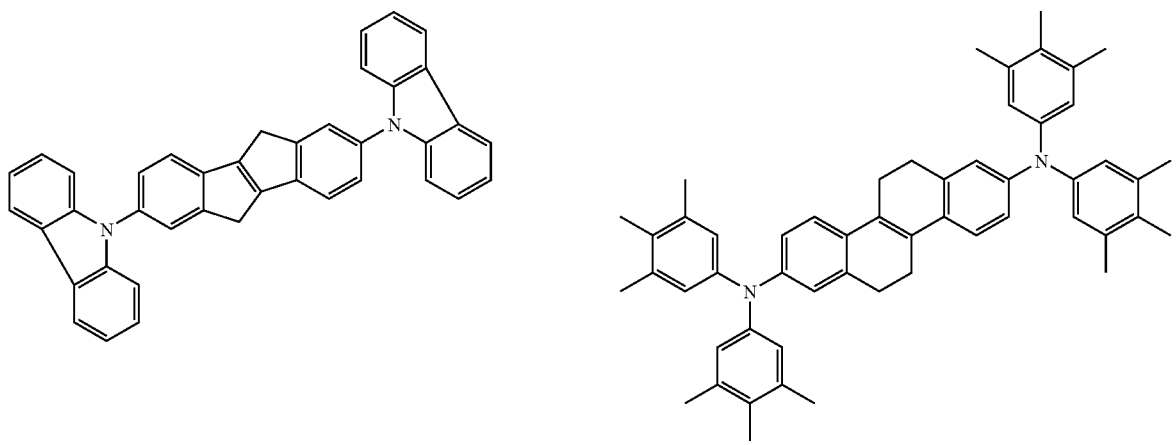
D-2-9
D-3-1
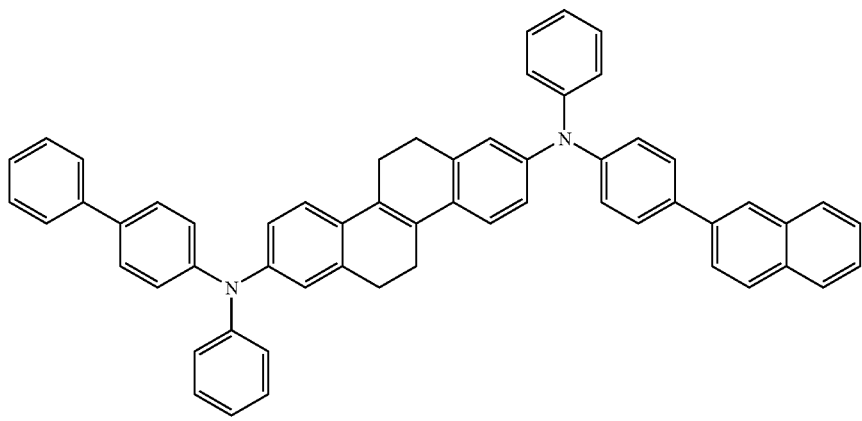
D-3-2

-continued
D-3-3
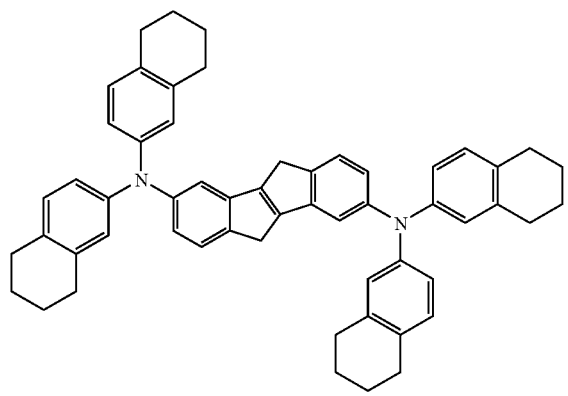
D-3-4
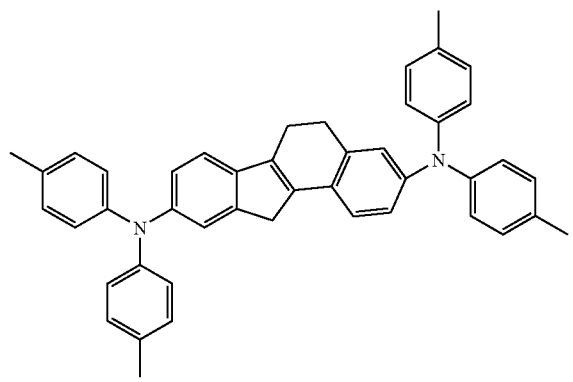
D-3-5
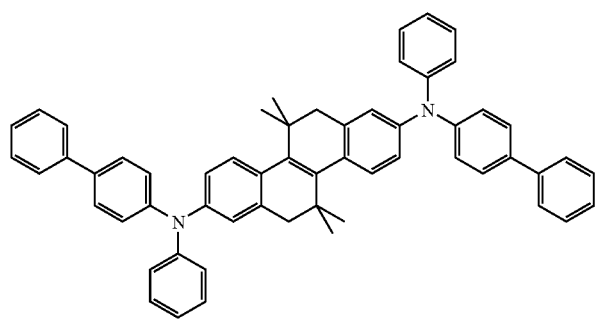
D-3-6
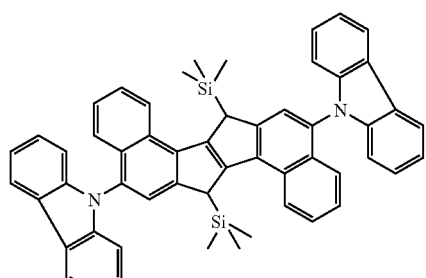
D-3-7
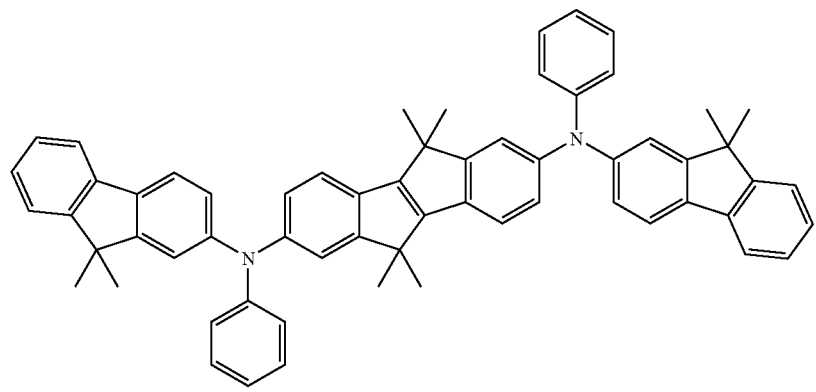

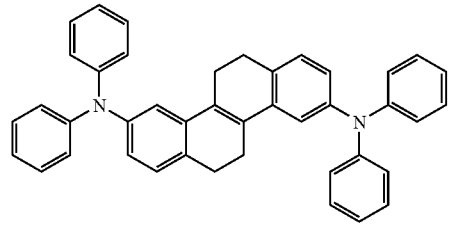
D-3-8
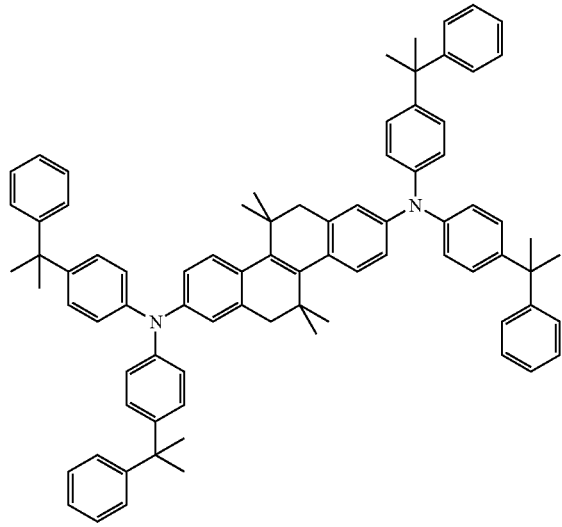
D-3-9
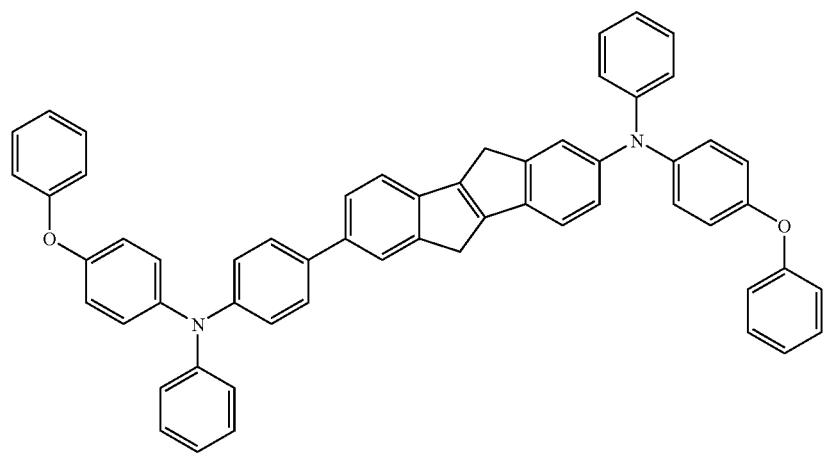
D-4-1
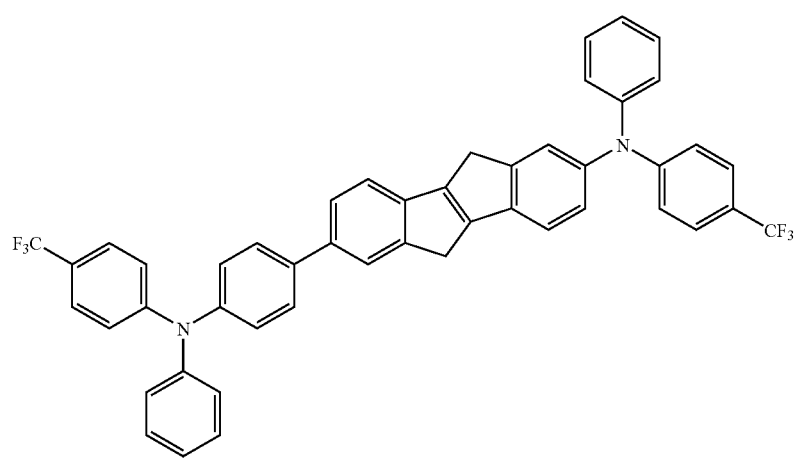
D-4-2

D-4-3
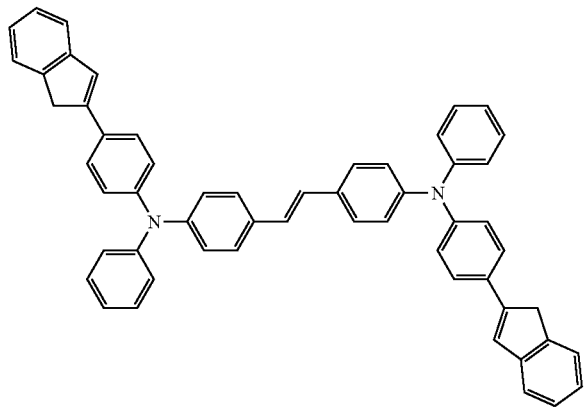
D-4-4
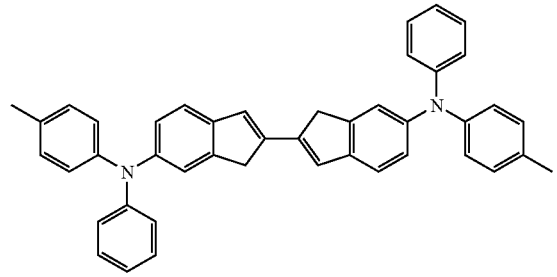
D-4-5
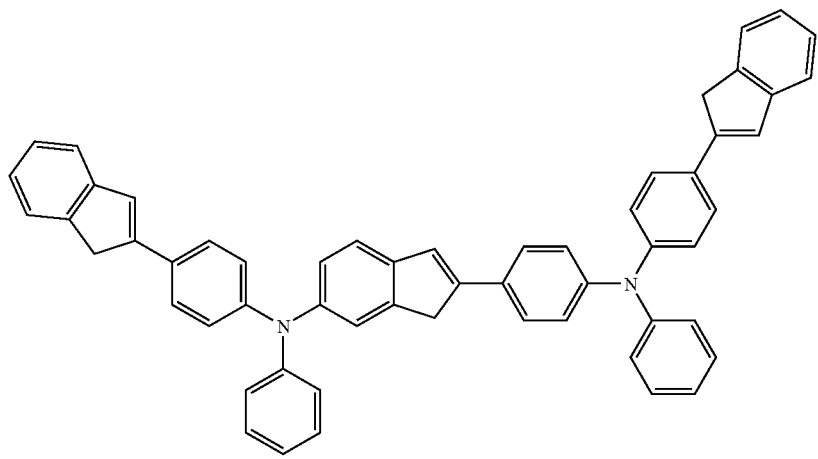
D-4-6
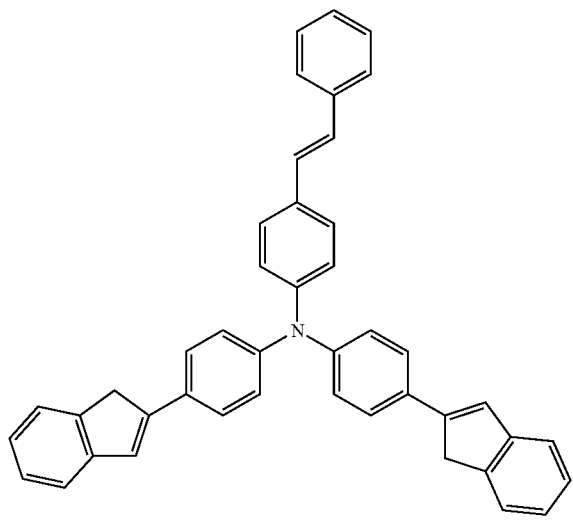
D-5-1
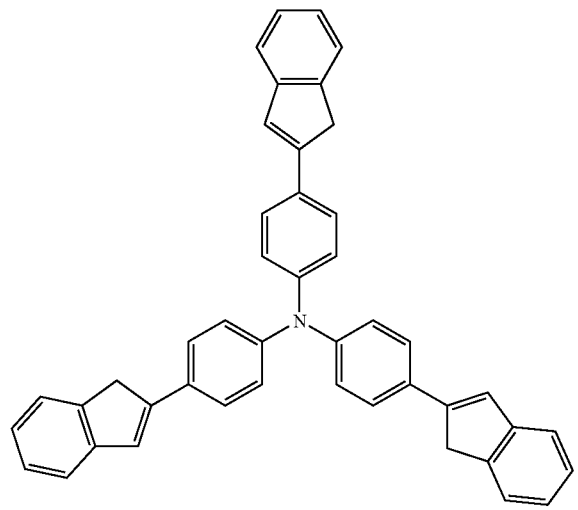

-continued
D-5-2
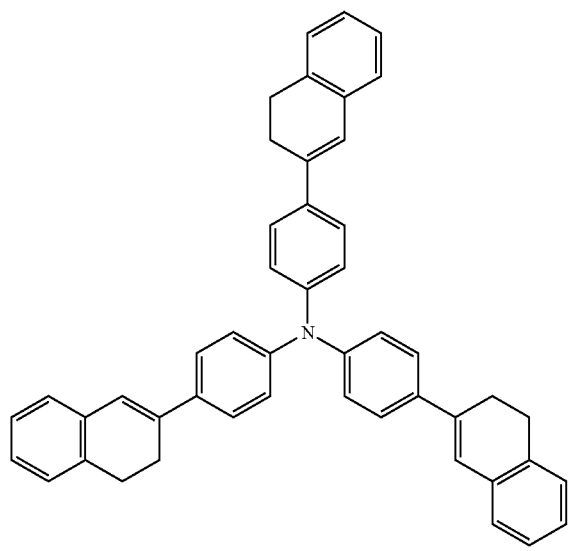
D-5-3
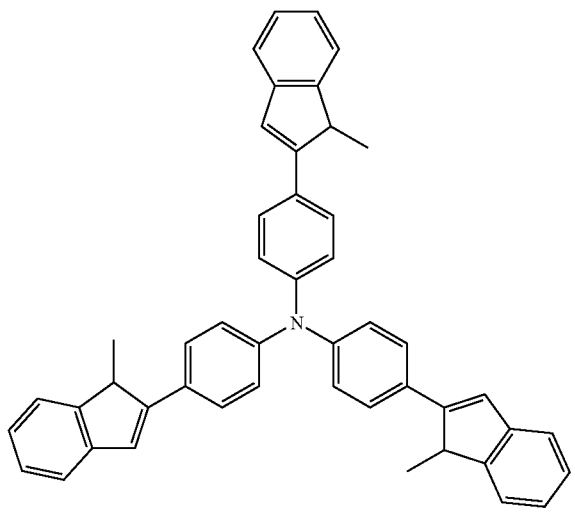
D-5-3
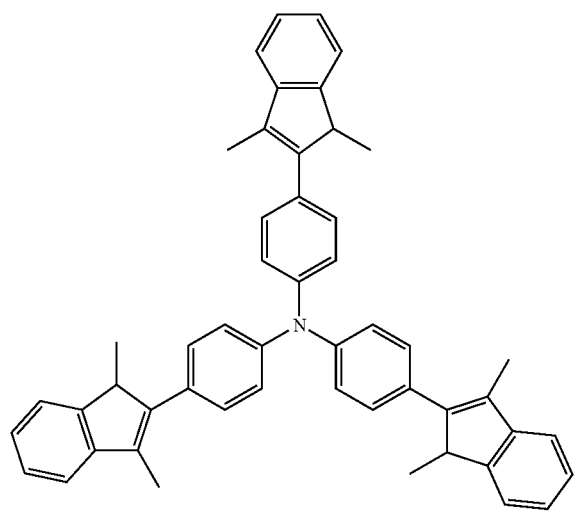
D-5-4
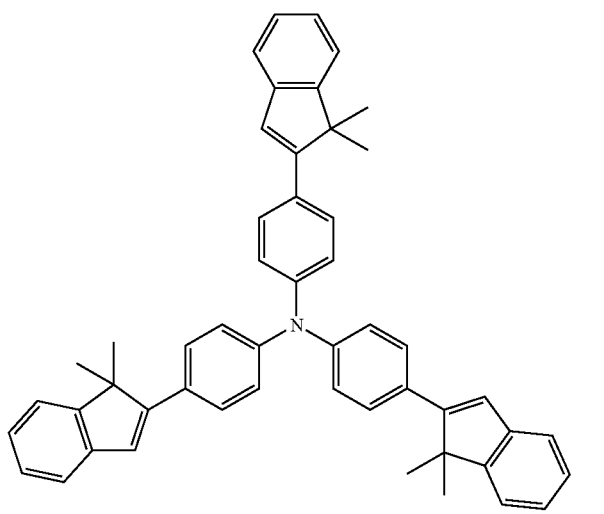
D-5-5
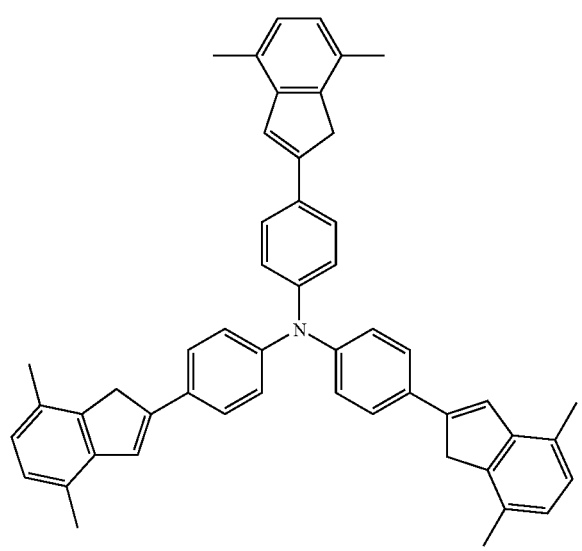
D-5-6
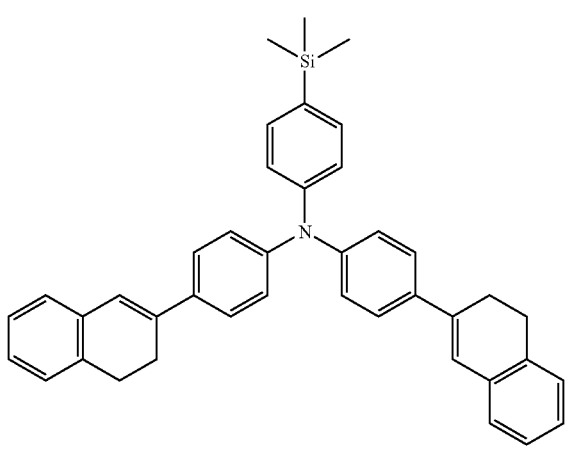

-continued
D-5-7
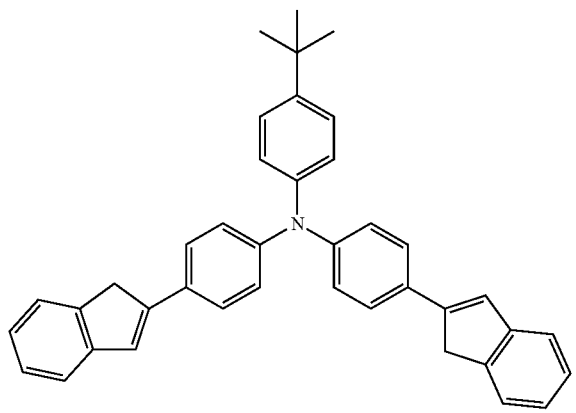
D-5-8
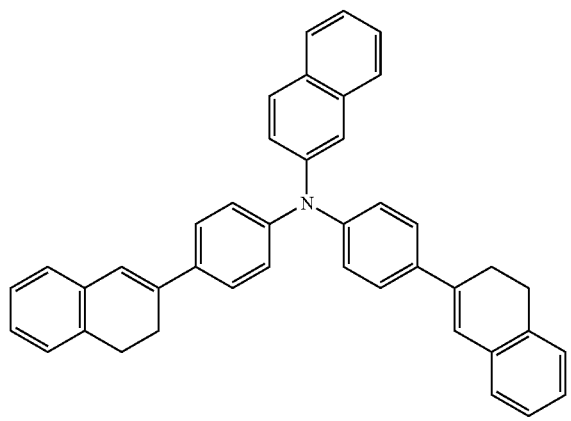
D-6-1
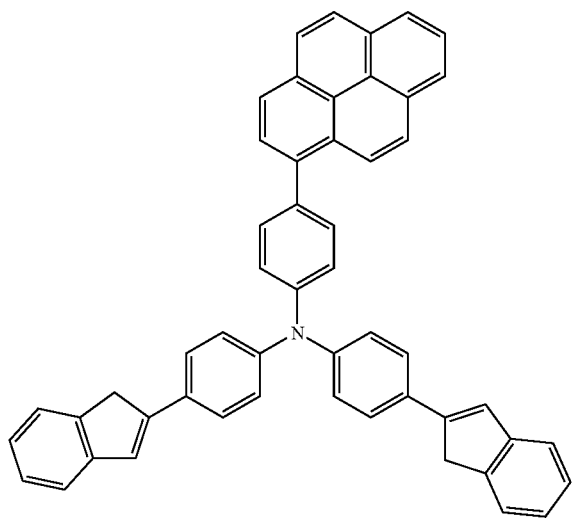
D-6-2
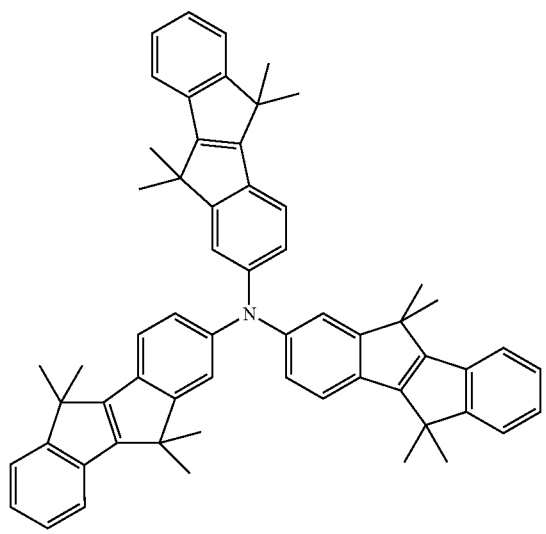
D-6-3
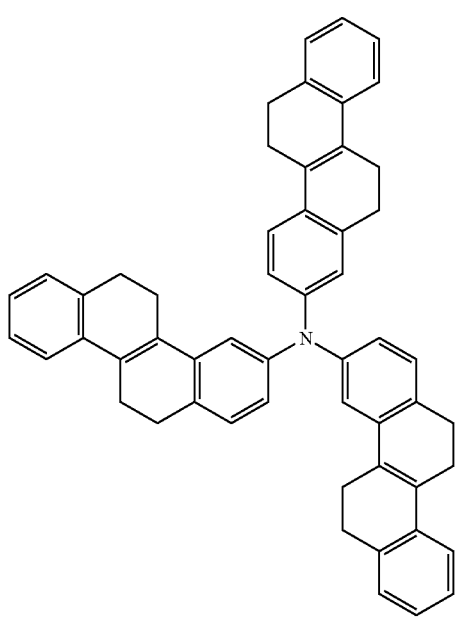

-continued
D-6-4
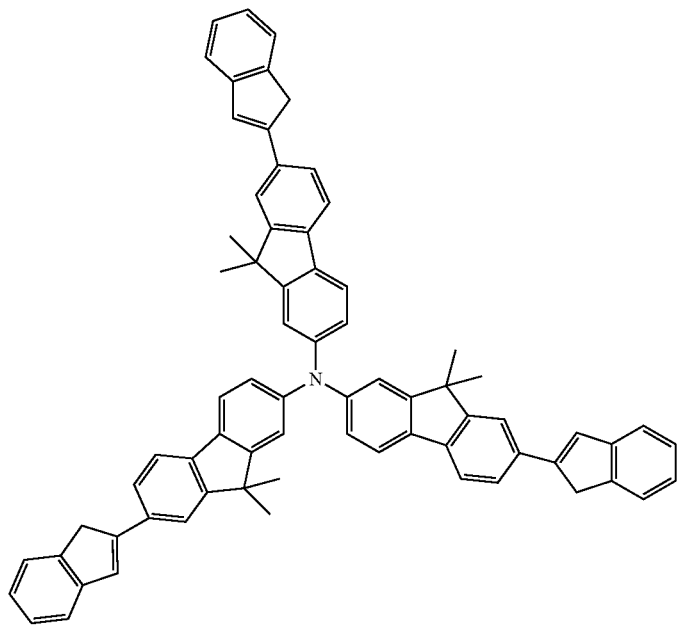
D-6-5
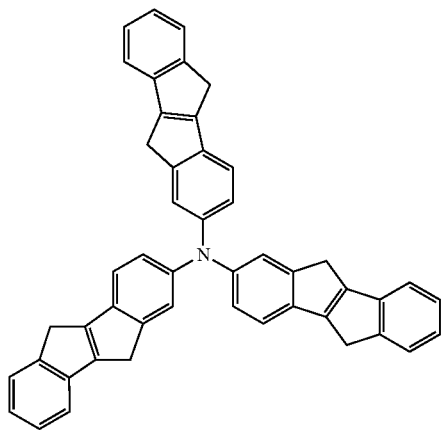
D-6-6
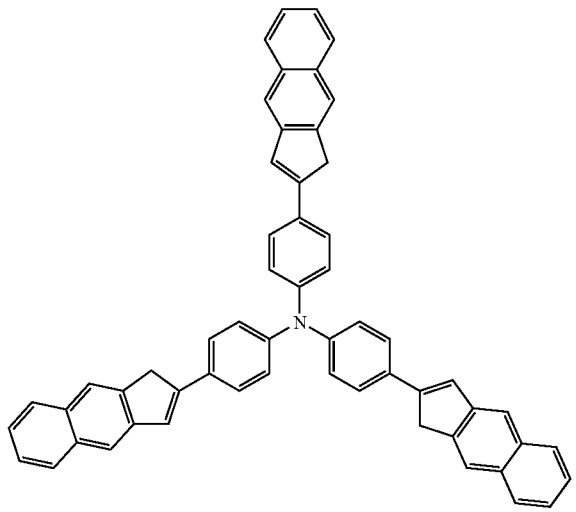
D-7-1
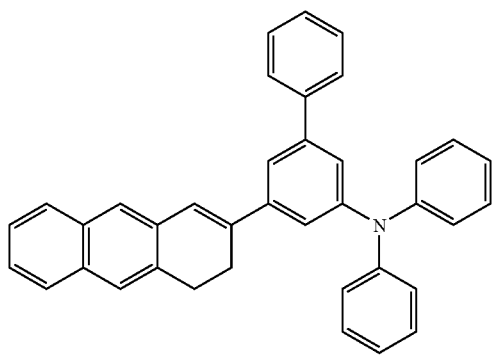
D-7-2
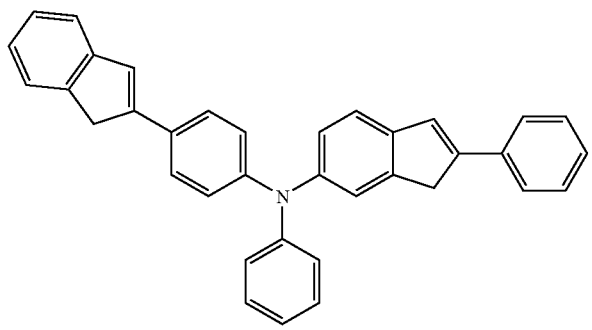

-continued

D-7-3
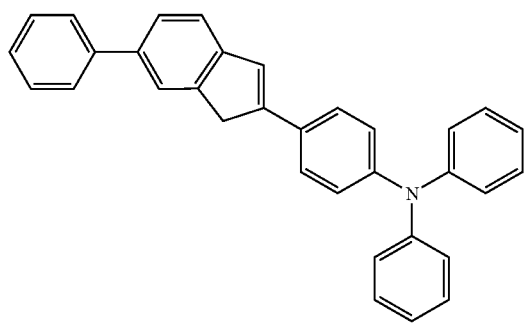

D-7-4
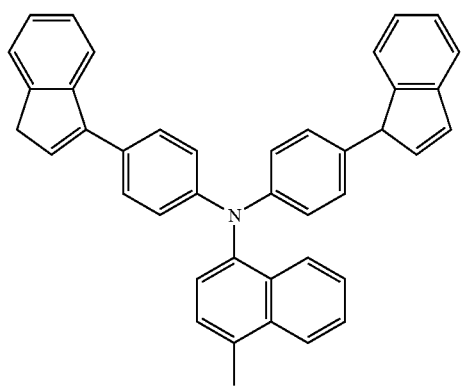

D-7-5
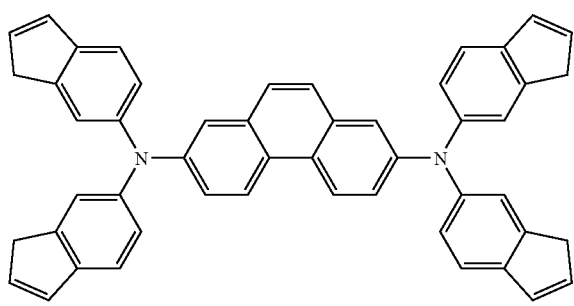

D-7-6
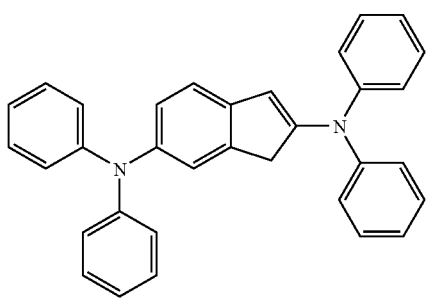

D-7-7
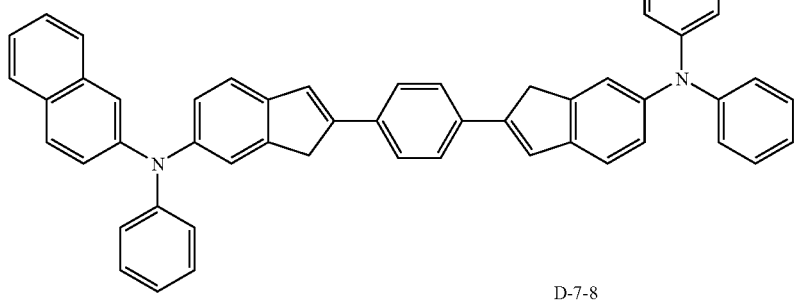

D-7-8
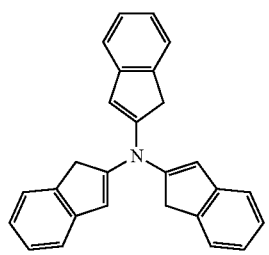

D-7-9
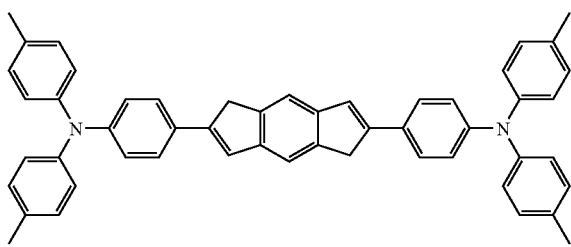

Following is a description regarding a preparing process about the aromatic amine derivative of the present invention.

The preparation process of the aromatic amine derivative represented by general formula (I) of the present invention is not particularly limited and may be in accordance with well-known process, for example, synthesizing aromatic amine from arylhalide and amine compound which is described in Angew. Chem. Int. Ed. Engl. 12, 1348 (1995); Japanese Unexamined Patent Application Laid-Open No. 10-1239742; J. Org. Chem., 61, 1133 (1996) and J. Am. Chem. Soc., 118, 7215 (1996); or synthesizing aromatic amine from aryltriflate and amine compound which is described in J. Org. Chem., 65, 1158 (2000), etc.

The aromatic amine derivative represented by the general formula (I) of the present invention reduces the wavelength of light emission and fairly enhances color purity of blue light emission because it adopts a structure making conjugate sites into a ring expressed by tetrahydrochrysene, dihydronaphthalene, indene, indenoindene, etc. Moreover, the aromatic amine derivative of the present invention has strong fluorescent property in its solid state, superior in an electric field electroluminescent property and further fluorescent quantum efficiency of 0.3 or greater. Still further, because it has a superior hole injection property or a superior hole transportation property from a metal electrode or from an organic thin layer, and a superior electron injection property or a superior electron transportation property from the metal electrode or from the organic thin layer, it is effectively employed as an light emitting material, particularly as a doping material for an organic EL device. Moreover, still other hole transporting material, electron transporting material or doping material may be employed.

The organic EL device of the present invention is a device comprising one or more organic thin film layers sandwiched between an anode and a cathode. When the organic film has a single layer, a light emitting layer is sandwiched between the anode and the cathode. The light emitting layer comprises a light emitting material and may further comprise a hole injecting material or an electron injecting material to transport holes injected from the anode or electrons injected from the cathode, respectively, to the light emitting material. The aromatic amine derivatives of the present invention has an enhanced light emitting property and excellent hole injecting ability and hole transporting ability as well as excellent electron injecting ability and electron transporting ability and, therefore, can be used as a light emitting material or a doping material in the light emitting layer.

In the organic EL device of the present invention, the light emitting layer contains the aromatic amine derivative of the present invention in an amount of preferably 0.1 to 20% by weight and more preferably 1 to 10% by weight. Further, the aromatic amine derivatives of the present invention exhibit not only an extremely high fluorescent quantum efficiency but also high hole transporting ability and electron transporting ability, and further are capable of forming a uniform thin film, so that the light emitting layer may be formed from the aromatic amine derivatives only.

On the other hand, in the case where the organic EL device of the present invention includes two or more organic thin film layers having at least the light emitting layer which are sandwiched between the cathode and anode, the organic thin film layers preferably include an organic layer containing the aromatic amine derivative of the present invention as an essential component which is provided between the anode and the light emitting layer. Such an organic layer may be a hole injecting layer, a hole transporting layer, etc.

Further, in a case where the aromatic amine derivative of the present invention is employed as a doping material it is preferable that at least one kind selected from the group consisting of anthracene derivatives of a following general formula (VIII), anthracene derivatives of a following general formula (IX) and pyrene derivatives of a following general formula (X) is employed as a host material.

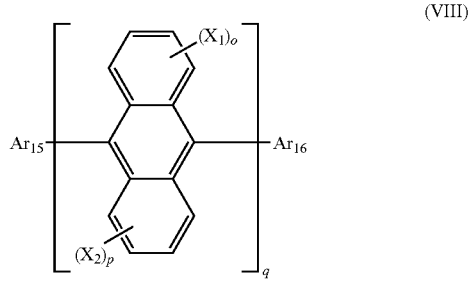

(VIII)

In the general formula (VIII), $X_1$ and $X_2$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms or a halogen atom; o and p each independently represents an integer of 0 to 4; when o and/or p is 2 or greater, plural of $X_1$ and/or $X_2$ may be the same with or different from each other. $Ar_{15}$ and $Ar_{16}$ each independently represents a substituted or unsubstituted aryl group having 5 to 50 ring carbon atoms or a substituted or unsubstituted heterocyclic group having 5 to 50 ring carbon atoms; at least one of $Ar_{15}$ or $Ar_{16}$ represents a substituted or unsubstituted fused ring aryl group having 10 to 50 ring carbon atoms or a substituted or unsubstituted aryl group having 10 or more carbon atoms; and q represents an integer of 1 to 3. When q is 2 or greater, a group within a parentheses [ ]:

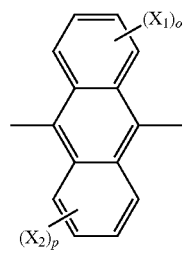

may be the same with or different from each other.

Specific examples and substituents of the $X_1$, $X_2$, $Ar_{15}$ and $Ar_{16}$ are the same as those explained about the foregoing general formula (I).

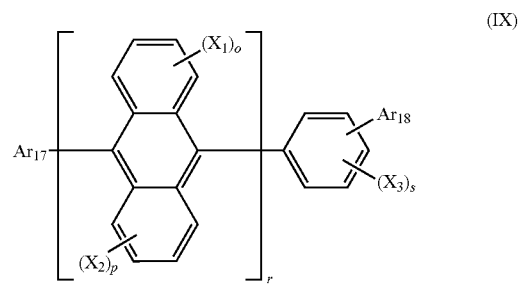

(IX)

In the general formula (IX), $X_1$ to $X_3$ are the same as $X_1$ and $X_2$ defined in the above general formula (VIII). o, p and/or a each independently represents an integer of 0 to 4; when o, p and/or a is 2 or greater, $X_1$, $X_2$ and/or $X_3$ may be the same with or different from each other; $Ar_{17}$ represents a substituted or unsubstituted fused ring aryl group having 10 to 50 ring carbon atoms; $Ar_{18}$ represents a substituted or unsubstituted aryl group having 5 to 50 ring carbon atoms; and r represents an integer of 1 to 3. When r is 2 or greater, a group within a parentheses [ ]:

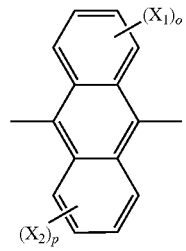

may be the same with or different from each other.

Specific examples and substituents of the $X_1$ to $X_3$, $Ar_{17}$ and $Ar_{18}$ are the same as those explained about the foregoing general formula (I).

Specific examples of anthracene derivative represented by the general formulae (VIII) and (IX) will be shown below, though not particularly limited thereto.

AN1
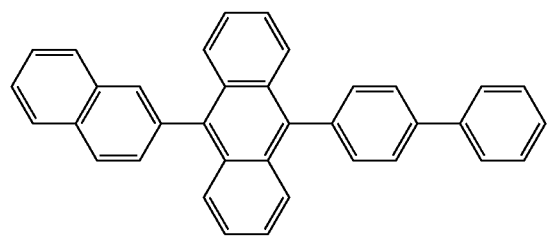
AN2
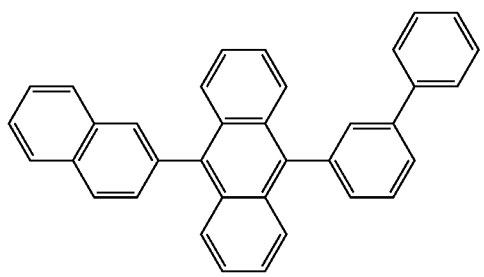
AN3
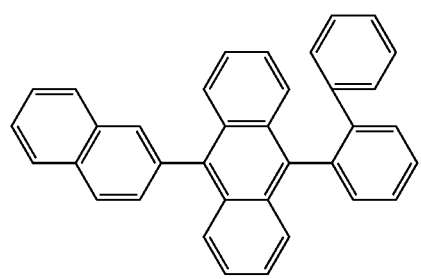
AN4
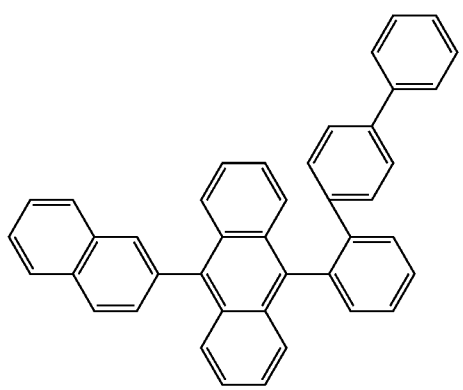
AN5
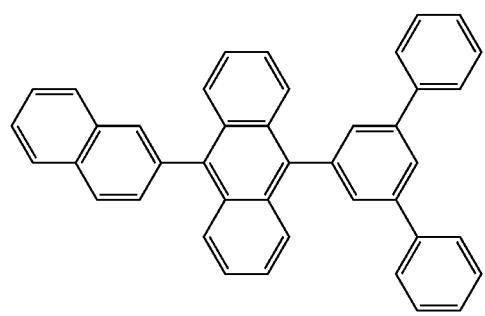
AN6
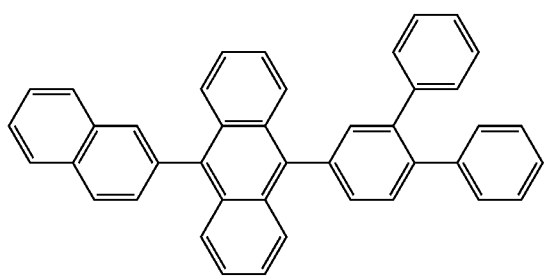
AN7
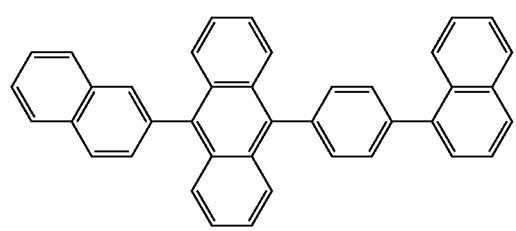
AN8
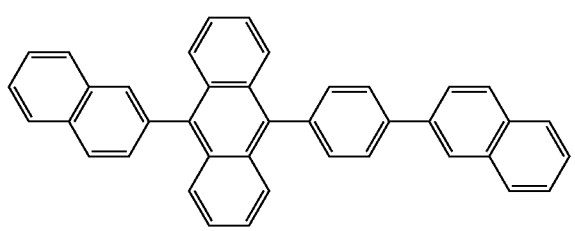

-continued
AN9
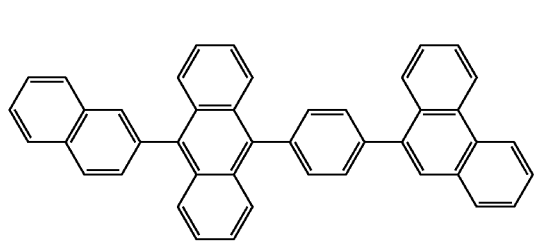
AN10
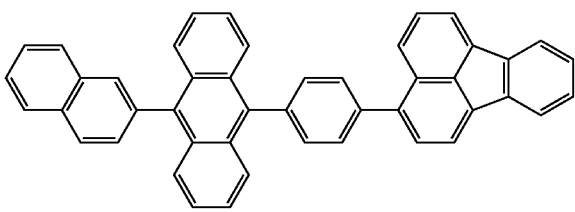
AN11
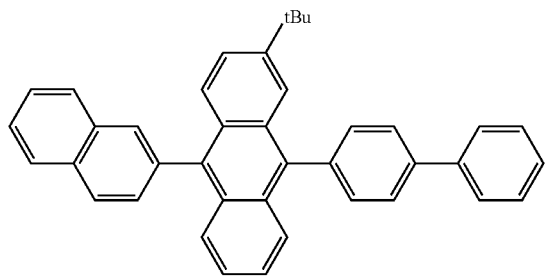
AN12
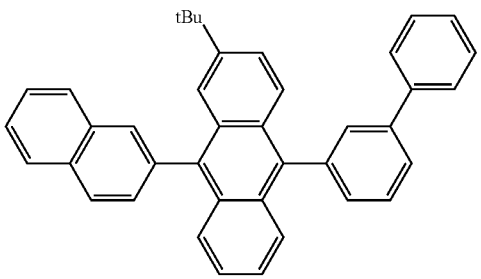
AN13
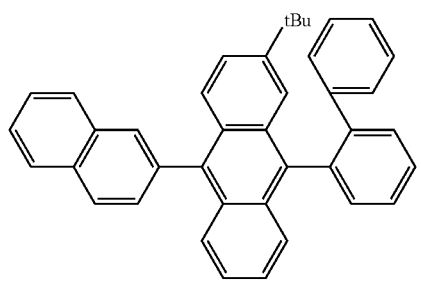
AN14
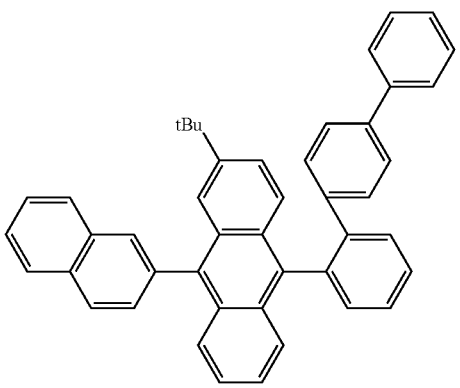
AN15
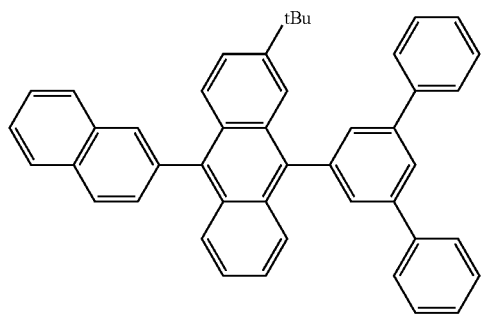
AN16
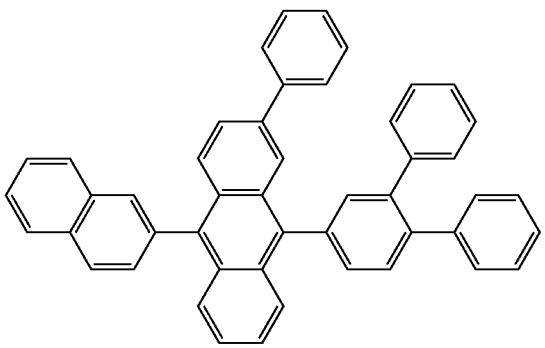

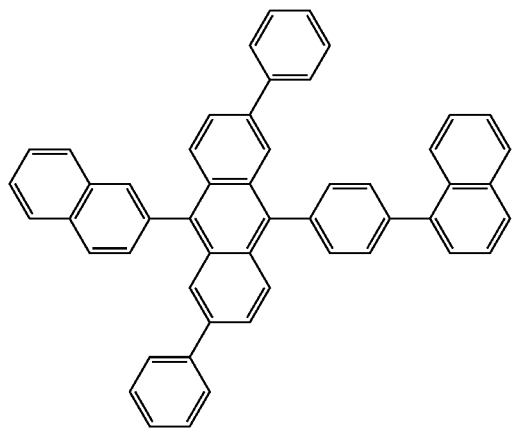

-continued
AN25
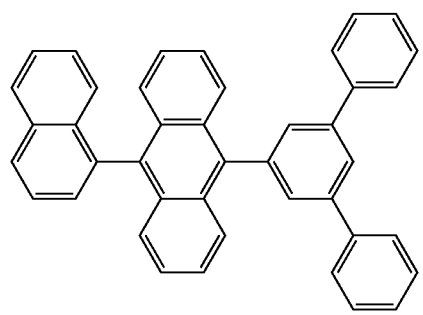
AN26
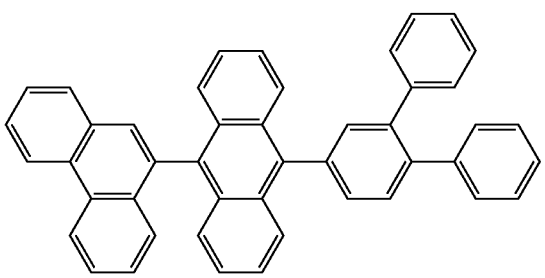
AN27
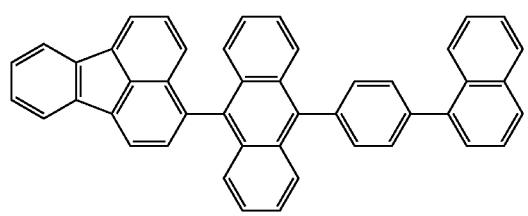
AN28
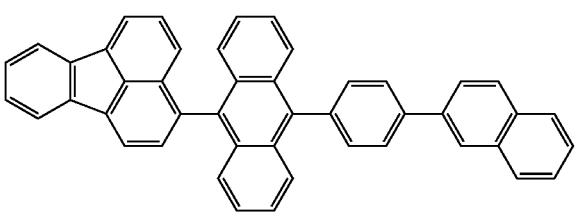
AN29
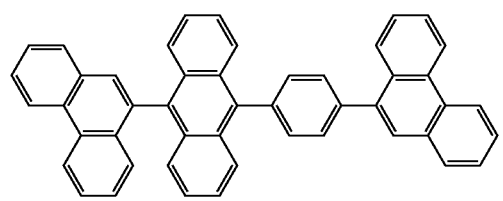
AN30
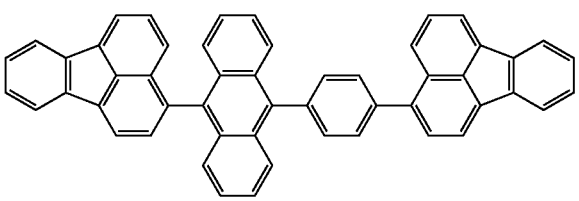
AN31
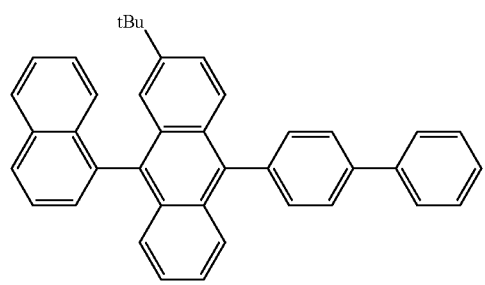
AN32
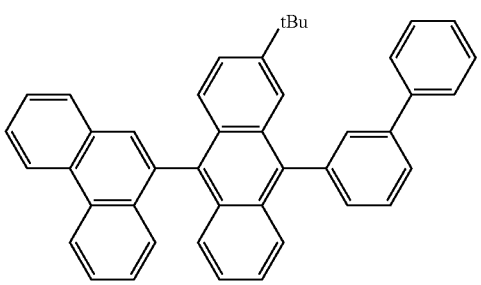
AN33
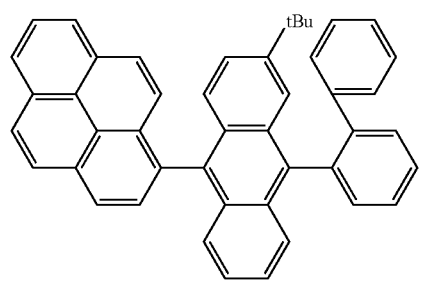
AN34
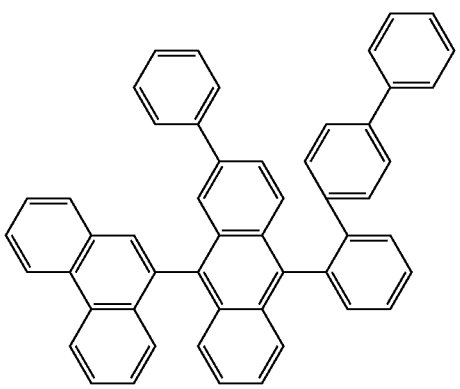

-continued
AN35
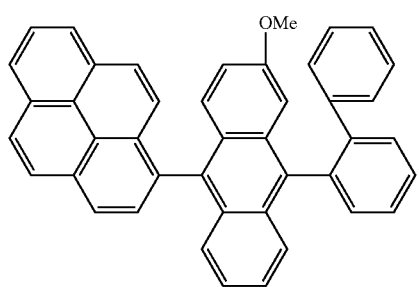
AN36
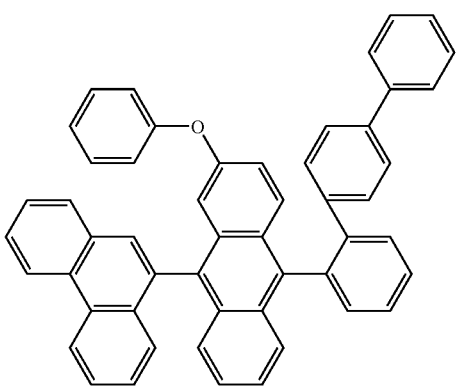
AN37
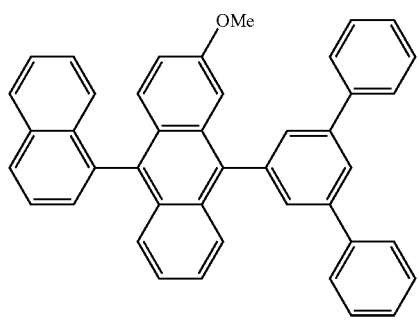
AN38
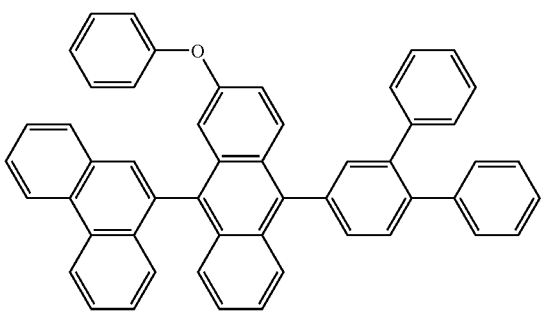
AN39
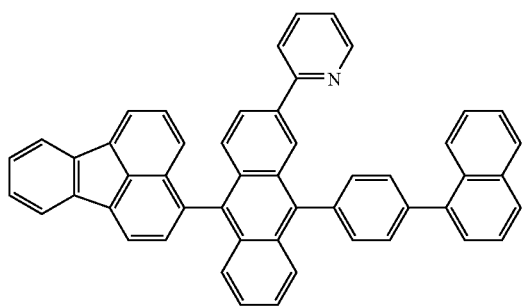
AN40
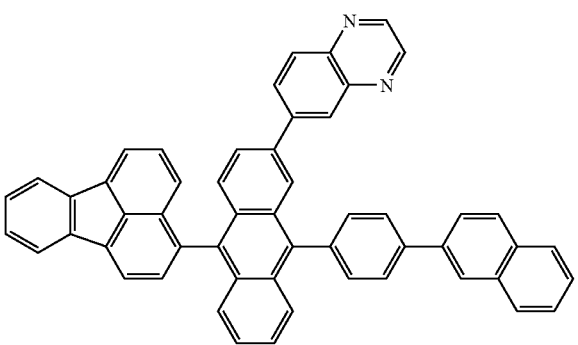
AN41
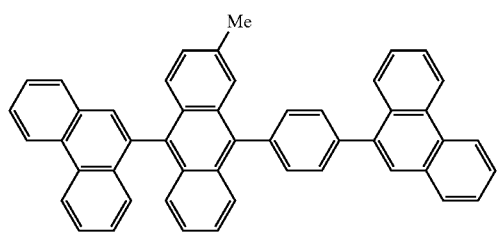
AN42
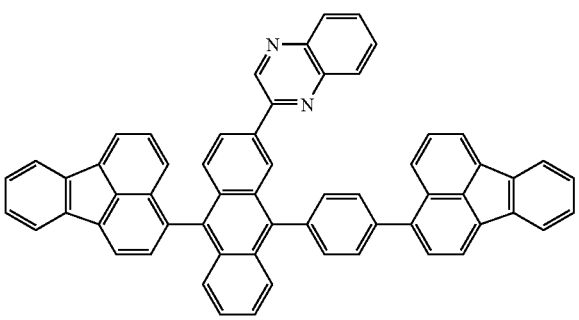

-continued

AN43
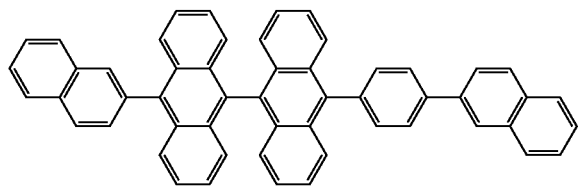

AN44
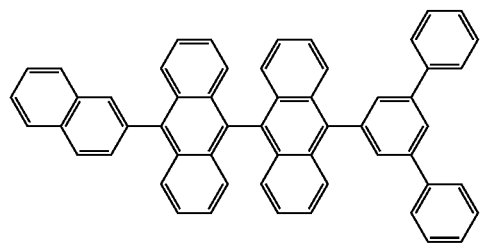

AN45
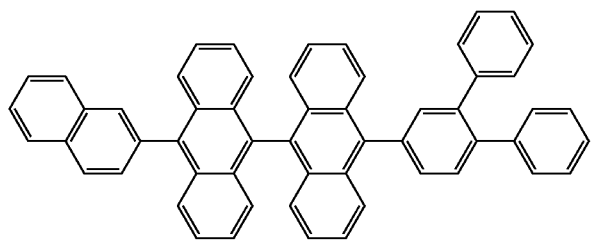

AN46
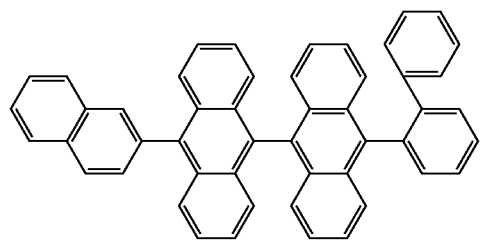

AN47
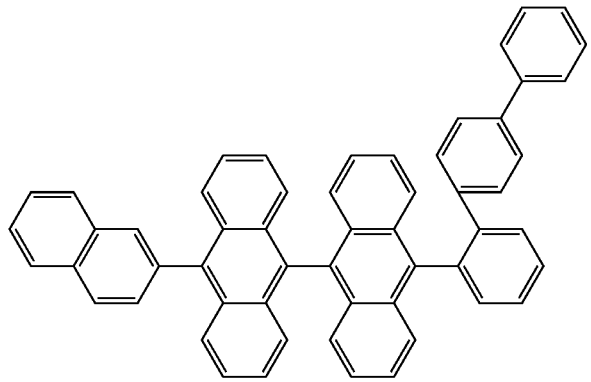

AN48
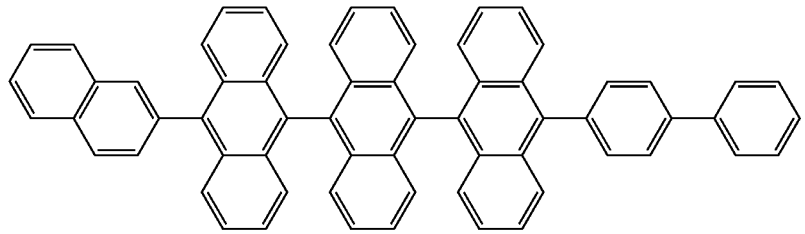

(X)
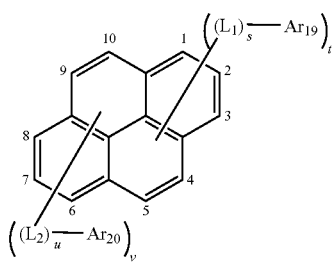

In the general formula (X), $Ar_{19}$ and $Ar_{20}$ each independently represent a substituted or unsubstituted aryl group having 5 to 50 ring carbon atoms; $L_1$ and $L_2$ each represents a substituted or unsubstituted phenylene group, a substituted or unsubstituted naphthalenylene group, a substituted or unsubstituted fluorenylene group or a substituted or unsubstituted dibenzosilolylene group; s represents an integer of 0 to 2, t represents an integer of 1 to 4, u represents an integer of 0 to 2 and v represents an integer of 1 to 4; further, $L_1$ or $Ar_{19}$ bonds to any one of 1 to 5 position of pyrene, also $L_2$ or $Ar_{20}$ bonds to any one of 6 to 10 position thereof; however, when t+v make an even number, $Ar_{19}$, $Ar_{20}$, $L_1$ and $L_2$ satisfy a following requirement (1) or a requirement (2):

(1) $Ar_{19}$ and $Ar_{20}$ represent a different group from each other, and/or $L_1$ and $L_2$ represent a different group from each other;

(2) When $Ar_{19}$ and $Ar_{20}$ represent the same groups each other and further, when $L_1$ and $L_2$ represent the same groups each other;

(2-1) s≠u and/or t≠v, or (2-2) When s=u and t=v, (2-2-1) Both $L_1$ and $L_2$ or pyrene each bonds respectively to different positions of $Ar_{19}$ and $A_{20}$, or (2-2-2) Both $L_1$ and $L_2$ are pyrene each bonds respectively to the same position of $Ar_{19}$ and $Ar_{20}$, excluding a case where a pyrene derivative having both $L_1$ and $L_2$ or both $Ar_{19}$ and $Ar_{20}$ bond to 1 and 6 positions thereof, or 2 and 7 positions thereof.

Specific examples and substituents of the $Ar_{19}$, $Ar_{20}$, $L_1$ and $L_2$ are the same as those explained about the foregoing general formula (I).

Specific examples of the pyrene derivative represented by the general formula (X) will be shown below, though not particularly limited thereto.

P1

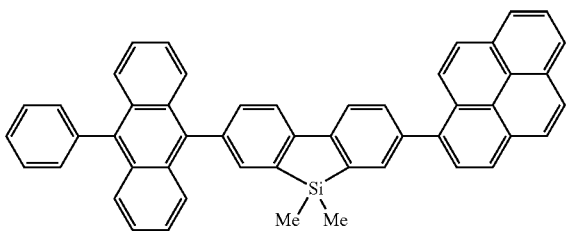

P2

P3

P4

P5

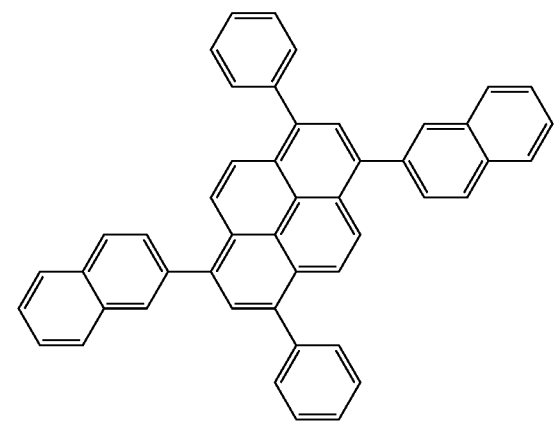

P6

P7

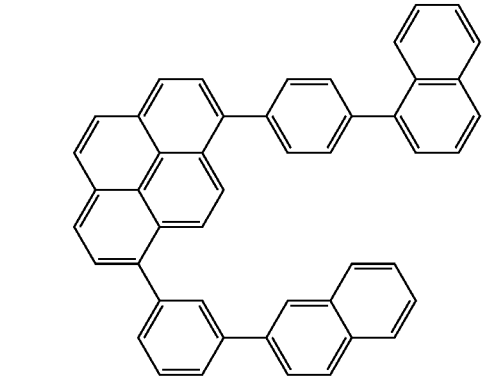

P8

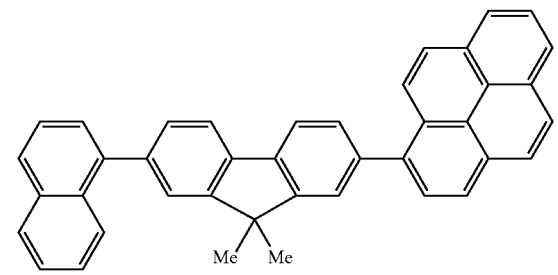

P9

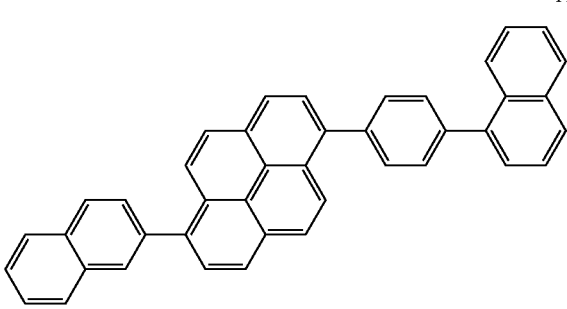

P10, P11, P12, P13, P14, P15, P16, P17, P18, P19

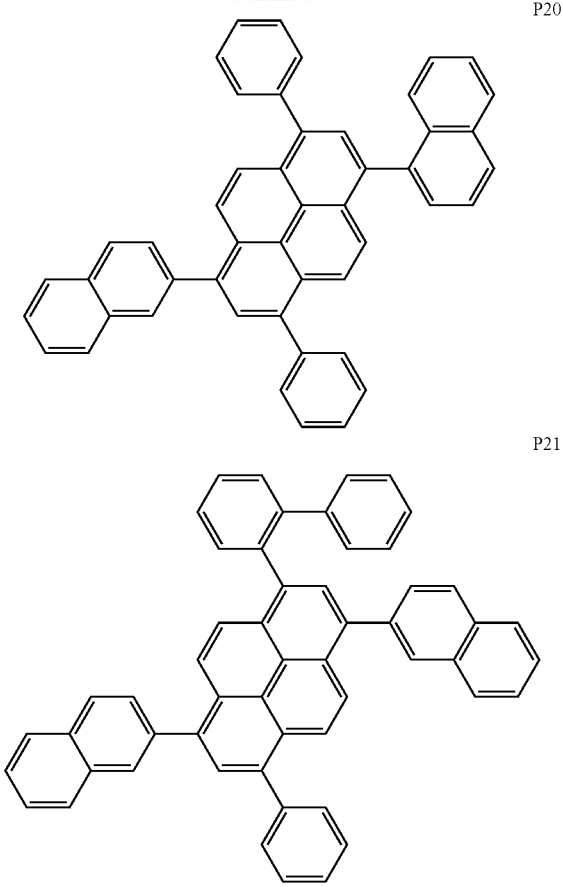

In the present invention, examples of the organic EL device of a multilayer type include those having laminated structures such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The multilayer may also optionally contain, in addition to the aromatic amine derivatives of the present invention, conventionally known materials such as light emitting materials, doping materials, hole injecting materials or electron injecting materials according to its requirements. The organic EL device having such a multilayer structure can be prevented from suffering from deterioration in luminance and lifetime due to quenching. If required, the light emitting materials, doping materials, hole injecting materials and electron injecting materials may be used in combination with each other. The use of the doping materials enables the resultant device to be improved in luminance and efficiency of light emission, and further emit a red color light or a blue color light. Further, in the organic EL device of the present invention, the hole injecting layer, the light emitting layer and the electron injecting layer may respectively have a laminated structure including two or more layers. In this occasion, the laminated hole injecting layer may include a hole injecting layer into which holes are injected from the electrode, and a hole transporting layer for accepting the holes from the hole injecting layer and transporting the holes to the light emitting layer. Also, the laminated electron injecting layer may include an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the organic thin film layers or the metal electrodes.

Examples of the host material or the doping material besides the foregoing general formulae (IX) to (XI) employable for the light emitting layer together with the aromatic amine derivative of the present invention include fused mass aromatic compound such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene, 1,4-bis(9'-ethynylanthracenyl)benzene; those derivatives; organometallic complex such as tris(8-quinolinolato)aluminium, bis-(2-methyl-8-quinolinolato)-4-(phenylphenolinato)aluminium, etc.; triarylamine derivative, styrylamine derivative, stilbene derivative, coumarin derivative, pyran derivative, oxazone derivative, benzothiazole derivative, benzoxazole derivative, benzimidazole derivative, pyrazine derivative, cinnamate ester derivative, diketopyrrolopyrrole derivative, acridone derivative, quinacridon derivative, etc.; though not particularly limited thereto.

The hole injecting material is preferably made of compounds which have a favorable hole transporting ability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazolethione, pyrazoline, pyrazolone, tetrahydroimidazole, hydrazone, acylhydrazone, polyarylalkanes, stilbene, butadiene, benzidine-type triphenylamine, styrylamine-type triphenylamine, diamine-type triphenylamine and derivatives thereof, as well as polyvinyl carbazoles, polysilanes, and polymer materials such as electrically conductive polymers, though not particularly limited thereto.

Of those hole injecting materials usable in the organic EL device of the present invention, more effective hole injecting materials are aromatic tertiary amine derivatives and phthalocyanine derivatives.

Specific examples of the aromatic tertiary amine derivatives include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane and so on, or oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O—GaPc, as well as naphthalocyanine derivatives, though not particularly limited thereto.

Also, in the organic EL device of the present invention, between the light emitting layer and the anode, there is preferably provided a layer containing these aromatic tertiary amine derivatives and/or phthalocyanine derivatives, such as the above hole transporting layer or hole injecting layer.

The electron injecting material is preferably made of compounds which have a favorable electron transporting ability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone and derivatives of these compounds. However, the electron injecting material is not limited to the compounds described above as the examples. Further, an electron accepting substance and an electron donating substance may be added to the hole injecting material and the electron injecting material, respectively, for enhanced sensitization thereof.

In the organic EL device of the present invention, among those electron injecting materials, more effective electron injecting materials are metal complex compounds and a five-member ring derivative having a nitrogen atom.

Specific examples of the metal complex compounds include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium, etc., though not particularly limited thereto.

The five-member ring derivatives having a nitrogen atom are preferably derivatives of oxazole, thiazole, oxadiazole, thiadiazole or triazole. Specific examples of the five-member ring derivatives having a nitrogen atom include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene, etc., though not particularly limited thereto.

In the organic EL device of the present invention, the light emitting layer may also optionally contain, in addition to the aromatic amine derivatives represented by the general formula (I), at least one material selected from the group consisting of light emitting materials, doping materials, hole injecting materials and electron injecting materials. Further, the organic EL device of the present invention may be further provided on a surface thereof with a protective layer, or the entire part thereof may be protected with silicone oil, resins, etc., in order to enhance stability thereof against temperature, humidity, atmosphere, etc.

The anode of the organic EL device according to the present invention may be suitably made of an electrically conductive material having a work function of exceeding 4 eV. Examples of the electrically conductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic electrically conductive resins such as polythiophene and polypyrrole. The cathode of the organic EL device according to the present invention may be suitably made of an electrically conductive material having a work function of 4 eV or smaller. Examples of the electrically conductive material for the cathode include magnesium, calcium, tin, lead, titanium, yttrium, lithium, ruthenium, manganese, aluminum, lithium fluoride and alloys thereof, though not particularly limited thereto. Examples of the alloy include magnesium/silver alloys, magnesium/indium alloys and lithium/aluminum alloys. However, the alloy is not limited to the alloys described above as the examples. The composition of the alloy is controlled by the temperature of the sources of vapor deposition, the atmosphere and the degree of vacuum and is selected suitably. The anode and cathode may be constituted of two or more layers, if required.

At least one surface of the organic EL device of the present invention preferably exhibits a sufficient transparency in a wavelength range of light emitted therefrom in order to enhance an efficiency of light emission thereof. Further, it is preferable that the substrate is also transparent. The transparent electrode is formed using the above electrically conductive material by vapor deposition process, sputtering process, etc., so as to ensure a desirable transparency thereof. It is preferable that the electrode at the side of the light emitting face has a transmittance of the emitted light of 10% or greater. The substrate is not particularly limited as long as it suitably has a good mechanical and thermal strength as well as a good transparency. There are glass substrates and transparent films as the substrate. Examples of the transparent films include films of resins such as polyethylene, copolymers of ethylene and vinyl acetate, copolymers of ethylene and vinyl alcohol, polypropylene, polystyrene, polymethyl methacrylate, polyvinylchloride, polyvinylalcohol polyvinylbutyral, nylon, polyether ether ketones, polysulfones, polyethersulfones, copolymers of tetrafluoroethylene and perfluoroalkylvinyl ethers, polyvinyl fluoride, copolymers of tetrafluoroethylene and ethylene, copolymers of tetrafluoroethylene and hexafluoropropylene, polychlorotrifluoroethylene, polyvinylidene fluoride, polyesters, polycarbonates, polyurethanes, polyimides, polyetherimides, polyimides and polypropylene.

The respective layers in the organic EL device of the present invention may be formed by either a dry film-forming process such as vacuum deposition, sputtering, plasma and ion-plating, or a wet film-forming process such as spin-coating, dipping and flow-coating. It is necessary that the thickness of the film be adjusted within a suitable range. When the thickness of the film is thicker than the suitable range, it is necessary that a great voltage be applied to obtain a specific output of the light emission and the current efficiency decreases. When the thickness of the film is thinner than the suitable range, pin holes are formed and a sufficient luminance cannot be obtained when an electric field is applied. The suitable thickness of the respective layers is usually in the range of from 5 nanometers to 10 μm and preferably from 10 nanometers to 0.2 μm.

In the wet film-forming process, materials constituting the respective layers are dissolved or dispersed in a suitable solvent such as ethanol, chloroform, tetrahydrofuran and dioxane to form a thin film thereof. The solvent used for forming the respective layers is not particularly limited. In any of the layers of the organic thin films, suitable resins or additives may be used for improving the properties of the films and preventing formation of pin holes. Examples of the resins usable for the above purposes include insulating resins such as polystyrene, polycarbonates, polyarylates, polyesters, polyamides, polyurethanes, polysulfones, polymethylmethacrylate, polymethylacrylate and celluloses as well as copolymers thereof, photoconductive resins such as poly-N-vinylcarbazole and polysilanes, and electrically conductive resins such as polythiophene and polypyrrole. Examples of the additive include antioxidants, ultraviolet ray absorbents and plasticizers.

The organic EL device of the present invention is suitably applied to, for example, a planar light emitting member for a flat panel display of wall-hanging type television, a back light of copiers, printers and liquid crystal displays, a light source for instruments, a display panel and a beacon light. Further, the material of the present invention can be used not only for organic EL devices but also in other applications such as electrophotographic members, photoelectric converters, solar cells, image sensors, etc.

EXAMPLES

The present invention shall be explained below in further details with reference to examples.

Synthesis Example 1

Synthesis of Compound D-3-1

Under an atmospheric argon gas flow, 5,6,11,12-tetrahydrochrysene-2,8-diolbistrifluoromethanesulfonate prepared in a publicly known process (J. Org. Chem., 57,1262 (1992)) in an amount of 5.3 g (10 millimole), bis(3,4,5-trimethylphenyl)amine in an amount of 6.3 g (25 millimole), palladium acetate in an amount of 0.03 g (1.5% by mole), tri-t-butylphosphine in an amount of 0.06 g (3% by mole), t-butoxy sodium in an amount of 2.4 g (25 millimole) and dried toluene in an amount of 100 milliliter were placed into a three-neck flask equipped with a cooling pipe and having a capacity of 300 milliliter, and the resultant solution was stirred under heating at a temperature of 100° C. for one night. After the reaction was completed, precipitated crystal was separated by filtration and washed with the uses of 50 milliliter of toluene and 100 milliliter of methanol, and as a result, 6.2 g of pale yellow powder was obtained. The pale yellow powder was identified as Compound D-3-1 from the result in accordance with $^1$H-NMR spectrum (FIG. 1) and Field Desorption Mass Spectrum (FD-MS) measurement (yield: 85%). Further, the $^1$H-NMR spectrum was obtained by means of DRX-500 (Trade name; produced by Brucker Optics Inc.; deuterated methylene chloride solvent). Furthermore, the maximum fluorescent wavelength measured about the resultant compound among toluene solution was 437 nanometers.

Synthesis Example 2

Synthesis of Compound D-5-1

Figure 2:
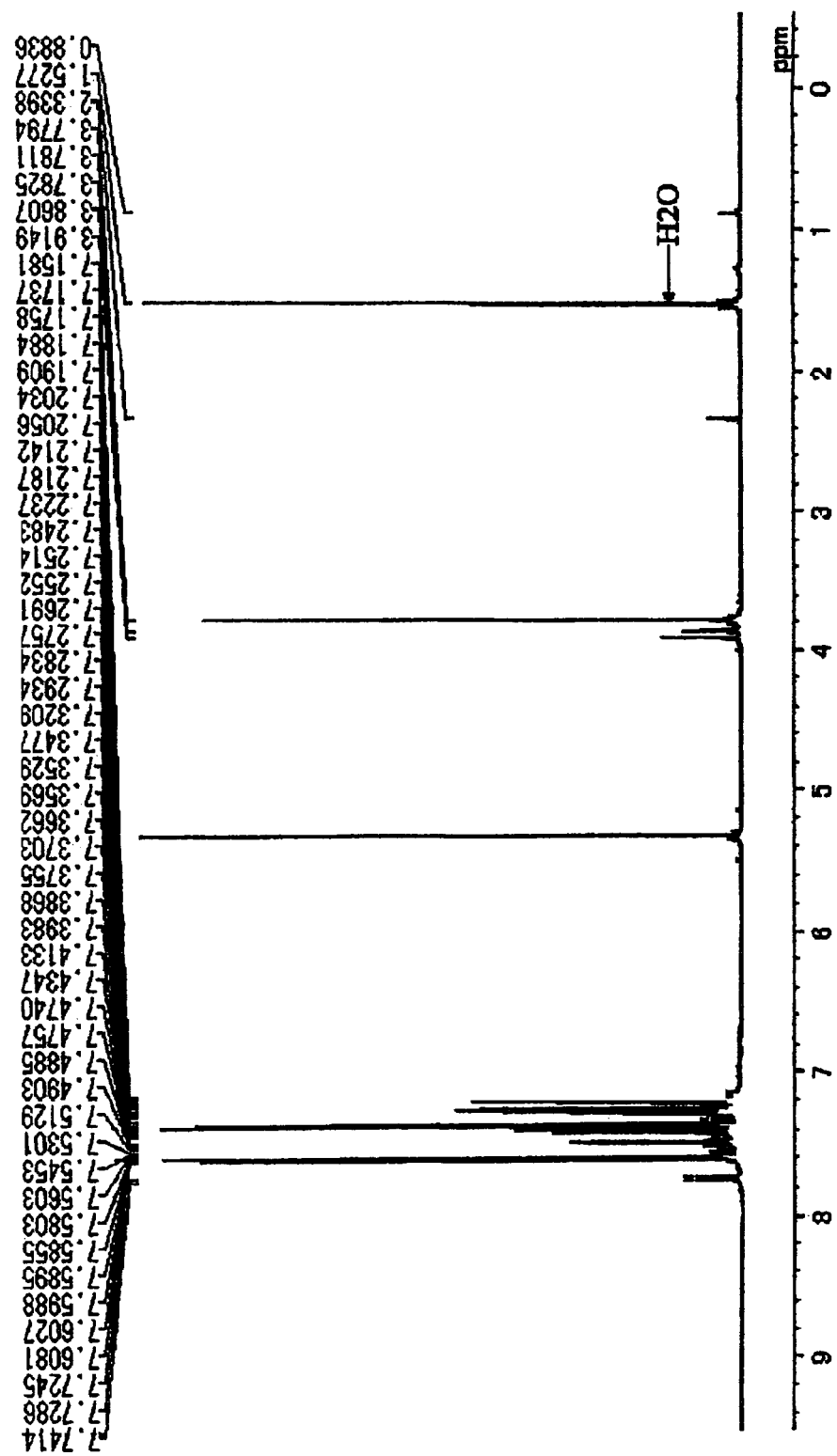
FIG. 2 is a chart showing $^1$H-NMR spectrum of the Compound D-5-1 being the aromatic amine derivative of the present invention obtained in Synthesis Example 2.

Under an atmospheric argon gas flow, 1H-indene-2-boronic acid prepared in a publicly known process (J. Org. Chem., 67,169 (2002)) in an amount of 9.8 g (62 millimole), tris(4-bromophenyl)amine in an amount of 8.2 g (17 millimole), (tetrakistriphenylphosphine)palladium in an amount of 0.4 g (0.34 millimole), sodium carbonate aqueous solution in an amount of 5.4 g (52 millimole, 2M) and dimethoxyethane in an amount of 50 milliliter were placed into a three-neck flask equipped with a cooling pipe and having a capacity of 300 milliliter, and the resultant solution was stirred under heating at a temperature of 100° C. for 8 hours. After the reaction was completed, precipitated crystal was separated by filtration and washed with the uses of 50 miter of water and 100 milliliter of methanol and then, purifying them by means of column chromatography (silicagel, developing solvent: hexane/methylene chloride=8/2), 6.6 g of pale yellow powder was obtained. The pale yellow powder was identified as Compound D-5-1 from the result of $^1$H-NMR spectrum (FIG. 2) and Field Desorption Mass Spectrum (FD-MS) measurement (yield: 67%). Further, the $^1$H-NMR spectrum was obtained by means of DRX-500 (Trade name; produced by Brucker Optics Inc.; deuterated methylene chloride solvent). Furthermore, the maximum fluorescent wavelength measured about the resultant compound among toluene solution was 433 nanometers.

Example 1

A 130 nanometers-thick transparent electrode made of indium tin oxide was formed on a glass substrate having a size of 25 mm×75 mm×1.1 mm. The glass substrate with the transparent electrode was cleaned by irradiation of ultraviolet ray and ozone. The thus cleaned glass substrate with the transparent electrode was mounted to a vacuum vapor deposition apparatus.

First, N',N"'-bis[4-(diphenylamino)phenyl]-N',N"'-diphenylbiphenyl-4,4'-diamine was vapor-deposited to form a hole injecting layer having a thickness of 60 nanometers, and then N,N,N',N'-tetrakis(4-biphenyl)-4,4'-benzidine was vapor-deposited on the hole injecting layer to form a hole transporting layer having a thickness of 20 nanometers. Then, 10-(4-(naphthalene-2-yl)phenyl)-9-(naphthalene-2-yl)anthracene as a host material and the above Compound D-3-1 as a doping material were simultaneously vapor-deposited at a weight ratio of 40:2 on the hole transporting layer to form a light emitting layer having a thickness of 40 nanometers.

Next, tris(8-hydroxyquinolinato)aluminum was vapor-deposited on the light emitting layer to form an electron injecting layer having a thickness of 20 nanometers. Subsequently, lithium fluoride was vapor-deposited up to 1 nanometer in thickness and then, aluminum was vapor-deposited up to 150 nanometers in thickness. The aluminum/lithium fluoride layer works as a cathode. An organic EL device was fabricated in the manner descried above.

As a result of subjecting the resultant organic EL device to a test by feeding electric current, it was confirmed that a pure blue light with a luminance of 201 cd/m$^2$ (peak wavelength of light emission:, 450 nanometers) and current efficiency of 2.0 cd/A was emitted at a voltage of 6.5 V and a current density of 10 mA/cm$^2$.

Example 2

An organic EL device was fabricated in accordance with the same procedures as those conducted in Example 1 except that Compound D-3-1 was replaced with Compound D-1-4.

As a result of subjecting the resultant organic EL device to a test by feeding electric current, it was confirmed that a pure blue light with a luminance of 172 cd/m$^2$ (peak wavelength of light emission: 444 nanometers) and current efficiency of 1.7 cd/A was emitted at a voltage of 6.5 V and a current density of 10 mA/cm$^2$.

Comparative Example 1

An organic EL device was fabricated in accordance with the same procedures as those conducted in Example 2 except that Compound D-1-4 was replaced with N,N,N',N'-tetrakis (2-naphthyl)-4,4'-diaminostilbene.

As a result of subjecting the resultant organic EL device to a test by feeding electric current, it was confirmed that a blue light having a deteriorated poor purity with peak wavelength: 455 nanometers of light emission was emitted at a voltage of 6.5 V and a current density of 10 mA/cm$^2$.

From the above-mentioned result, it is verified that a luminescent center of stilbene skeleton induces a light emission of a long-wavelength and as a result, deteriorates the color purity of blue light emission.

Industrial Applicability

As explained above in detail, the organic EL device using the aromatic amine derivative according to the present invention exhibits excellent luminance of light emission under a low applied voltage, obtaining an enhanced efficiency of light emission and further, the device is free from deterioration in properties even after being used for a long period of time and, therefore, has a prolonged lifetime. The organic EL device of the present invention can be used, for example, for a planar light emitting member for a flat panel display of wall-hanging type television, a back light of copiers, printers and liquid crystal displays, a light source for instruments, a display panel and a beacon light. Further, the material of the present invention can be employed not only in the field of the organic EL device but also in the field of electrophotographic photosensitive member, photoelectric transducer, solar cell, image sensor, etc.

The invention claimed is:

1. An aromatic amine derivative represented by formula (IV):

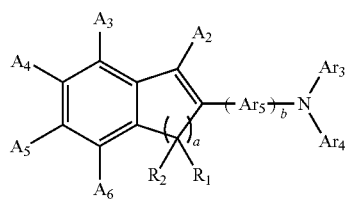

wherein $A_2$ to $A_6$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms or a substituted or unsubstituted heterocyclic group having 5 to 50 ring carbon atoms;

a couple of $A_3$ and $A_4$, a couple of $A_4$ and $A_5$, and a couple of $A_5$ and $A_6$ may bond to each other to form a saturated or unsaturated ring;

$R_1$ and $R_2$ each independently represents a hydrogen atom, a substituted or unsubstituted alkyl group having 1 to 20 carbon atoms, a substituted or unsubstituted aryl group having 5 to 20 ring carbon atoms, a substituted or unsubstituted aralkyl group having 6 to 20 ring carbon atoms, a substituted or unsubstituted cycloalkyl group having 3 to 20 ring carbon atoms or a substituted or unsubstituted silyl group having 1 to 20 carbon atoms;

a represents an integer of 1 to 3; when a is 2 or greater, $R_1$ and $R_2$ may be the same with or different from each other;

$Ar_3$ and $Ar_4$ each independently represents a substituted or unsubstituted aryl group having 5 to 50 ring carbon atoms;

a couple of $Ar_3$ and $Ar_4$ may bond to each other to form a saturated or unsaturated ring;

$Ar_5$ is a bivalent group made by removing one hydrogen atom from a group selected from the group consisting of a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, and a substituted or unsubstituted heterocyclic group having 5 to 50 ring carbon atoms; and b represents an integer of 1 to 3; when b is 2 or greater, plural $Ar_5$s may be the same with or different from each other.

2. The aromatic amine derivative according to claim 1, wherein
at least one among $A_3$ to $A_6$ is a group represented by formula (II) or formula (III):

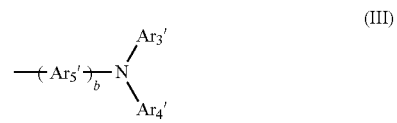

wherein $Ar_1'$ to $Ar_4'$ in formulae (II) and (III) each independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted heterocyclic group having 5 to 50 ring carbon atoms;

when $Ar_1'$ to $Ar_4'$ is formulae (II) and (III) are aryl groups, a couple of $Ar_1'$ and $Ar_2'$, and a couple of $Ar_3'$ and $Ar_4'$ may bond to each other to form a saturated or unsaturated ring;

$Ar_5'$ in formula (III) is any one of bivalent groups made by removing one hydrogen atom from each group to $Ar_1'$ to $Ar_4'$; and b in formula (III) represents an integer of 1 to 3; when b is 2 or greater, plural $Ar_5$'s may be the same with or different from each other.

3. An aromatic amine derivative represented by formula (V):

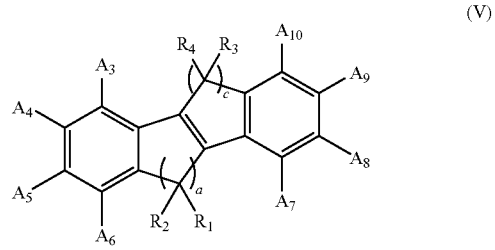

wherein $A_3$ to $A_{10}$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms or a substituted or unsubstituted heterocyclic group having 5 to 50 ring carbon atoms;

a couple of $A_3$ and $A_4$, a couple of $A_4$ and $A_5$, a couple of $A_5$ and $A_6$, a couple of $A_7$ and $A_8$, a couple of $A_8$ and $A_9$, and a couple of $A_9$ and $A_{10}$ may bond to each other to form a saturated or unsaturated ring;

$R_1$ to $R_4$ each independently represents a hydrogen atom, a substituted or unsubstituted alkyl group having 1 to 20 carbon atoms, a substituted or unsubstituted aryl group having 5 to 20 ring carbon atoms, a substituted or unsubstituted aralkyl group having 6 to 20 ring carbon atoms, a substituted or unsubstituted cycloalkyl group having 3 to 20 ring carbon atoms or a substituted or unsubstituted silyl group having 1 to 20 carbon atoms;

a and c each independently represents an integer of 1 to 3 respectively; when at least one of a or c is 2 or greater, at least one among plural of $R_1$ and $R_2$ or plural of $R_3$ and $R_4$ may be the same with or different from each other; wherein at least one among $A_3$ to $A_6$ and at least one among $A_7$ to $A_{10}$ is a group represented by formula (II) or formula (III)

(II)

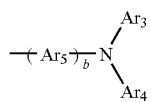

(III)

wherein $Ar_1$ to $Ar_4$ in formulae (II) and (III) each independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms or a substituted or unsubstituted heterocyclic group having 5 to 50 ring carbon atoms;

when $Ar_1$ to $Ar_4$ are aryl groups, a couple of $Ar_1$ and $Ar_2$, and a couple of $Ar_3$ and $Ar_4$ may bond to each other to form a saturated or unsaturated ring;

$Ar_5$ is any one of bivalent groups made by removing one hydrogen atom from each group to $Ar_1$ to $Ar_5$; and b represents an integer of 1 to 3; when b is 2 or greater, plural $Ar_5$s may by the same with or different from each other.

4. An aromatic amine derivative represented by formula (VI):

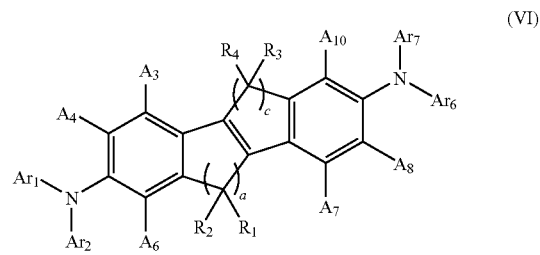

(VI)

wherein $A_3, A_4, A_6$ to $A_8$, and $A_{10}$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms or a substituted or unsubstituted heterocyclic group having 5 to 50 ring carbon atoms;

a couple of $A_3$ and $A_4$, and a couple of $A_7$ and $A_8$ may bond to each other to form a saturated or unsaturated ring;

$R_1$ to $R_4$ each independently represents a hydrogen atom, a substituted or unsubstituted alkyl group having 1 to 20 carbon atoms, a substituted or unsubstituted aryl group having 5 to 20 ring carbon atoms, a substituted or unsubstituted aralkyl group having 6 to 20 ring carbon atoms, a substituted or unsubstituted cycloalkyl group having 3 to 20 ring carbon atoms or a substituted or unsubstituted silyl group having 1 to 20 carbon atoms;

a and c each independently represents an integer 1 to 3 respectively; when at least one of a or c is 2 or greater, at least one among plural of $R_1$ and $R_2$ or plural of $R_3$ and $R_4$ may be the same with or different from each other; and $Ar_1, Ar_2, Ar_6$ and $Ar_7$ each independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms or a substituted or unsubstituted heterocyclic group having 5 to 50 ring carbon atoms;

when $Ar_1$ to $Ar_4$ are aryl groups, a couple of $Ar_1$ and $Ar_2$, and a couple of $Ar_3$ and $Ar_4$ may be bond each other to form a saturated or unsaturated ring.

5. An aromatic amine derivative represented by a following general formula (VII):

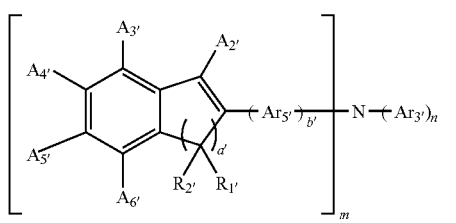

wherein $A_{2'}$ to $A_{6'}$ each independently represents a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms or a substituted or unsubstituted heterocyclic group having 5 to 50 ring carbon atoms;

a couple of $A_{3'}$ and $A_{4'}$, a couple of $A_{4'}$ and $A_{5'}$, and a couple of $A_{5'}$ and $A_{6'}$ may bond to each other to form a saturated or unsaturated ring $R_{1'}$ and $R_{2'}$ each independently represents a hydrogen atom, a substituted or unsubstituted alkyl group having 1 to 20 carbon atoms, a substituted or unsubstituted aryl group having 5 to 20 ring carbon atoms, a substituted or unsubstituted aralkyl group having 6 to 20 ring carbon atoms, a substituted or unsubstituted cycloalkyl group having 3 to 20 ring carbon atoms or a substituted or unsubstituted silyl group having 1 to 20 carbon atoms;

a' represents an integer of 1 to 3; when a' is 2 or greater, plural of $R_{1'}$ and $R_{2'}$ may be the same with or different from each other;

$Ar_{3'}$ independently represents a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms or a substituted or unsubstituted heterocyclic group having 5 to 50 ring carbon atoms;

$Ar_{5'}$ is any one of bivalent groups made by removing one hydrogen atom from each group of $Ar_{3'}$;

b' represents an integer of 1 to 3; when b' is 2 or greater, plural $Ar_{5'}$'s may be the same with or different from each other;

m represents an integer of 2 or 3, n represents an integer of 0 or 1, m+n equal 3; and further, plural of $A_{2'}$ to $A_{6'}$, $R_{1'}$, $R_{2'}$ or $Ar_{5'}$ may be the same with or different from each other.

6. The aromatic amine derivative according to claim 1, wherein $Ar_3$ and $Ar_4$ in formula (IV) each independently represents a substituted aryl group having 5 to 50 ring carbon atoms.

7. The aromatic amine derivative according to claim 1, wherein $Ar_3$ and $Ar_4$ in formula (IV) each independently represents an unsubstituted aryl group having 5 to 50 ring carbon atoms.

8. The aromatic amine derivative according to claim 3, wherein a and c are each 1 and each of $R_1$ to $R_4$ is a hydrogen atom.

9. The aromatic amine derivative according to claim 3, wherein each of $A_4$ and $A_8$ is a group represented by formula (II)

where each of $Ar_1$ and $Ar_2$ is a substituted aryl group having from 5 to 50 carbon atoms.

10. The aromatic amine derivative according to claim 3, wherein a is 1, c is 2 and each of $R_1$ to $R_4$ is a hydrogen atom.

11. The aromatic amine derivative according to claim 3, wherein
each of a and c is 2, and
each of $A_4$ and $A_8$ is a group represented by formula (II)

where each of $Ar_1$ and $Ar_2$ is an unsubstituted aryl group having from 5 to 50 carbon atoms.

12. The aromatic amine derivative according to claim 4, wherein a and c are each 2 and each of $R_1$ to $R_4$ are hydrogen.

13. The aromatic amine derivative according to claim 4, wherein each of $Ar_1$, $Ar_2$, $Ar_6$ and $Ar_7$ is a substituted aryl group having 5 to 50 carbon atoms.

14. The aromatic amine derivative according to claim 4, which is a compound represented by

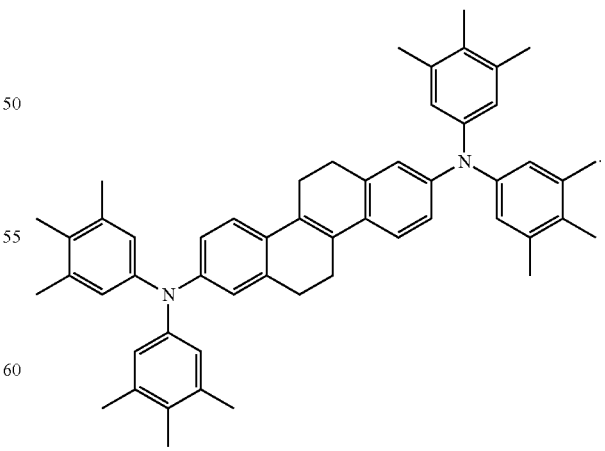

15. The aromatic amine derivative according to claim 4, which is a compound represented by

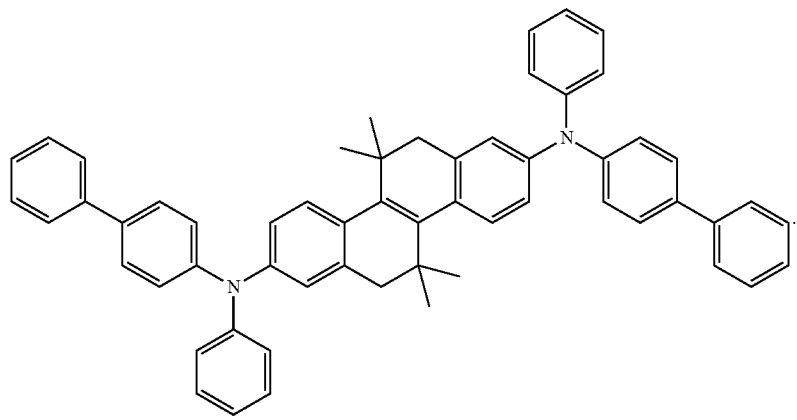

16. The aromatic amine derivative according to claim 5, wherein m is 3, n is 0 and each $Ar_{5'}$ group is a phenyl group.

17. The aromatic amine derivative according to claim 5, wherein each a' is 1, m is 3, n is 0, each $R_{1'}$ is a methyl group, each $R_{2'}$ is a hydrogen atom, and each $Ar_{5'}$ group is a phenyl group.

18. The aromatic amine derivative according to claim 5, wherein each a' is 2, m is 3, n is 0, each $R_{1'}$ and $R_{2'}$ group is a hydrogen atom, and each $Ar_{5'}$ group is a phenyl group.

19. The aromatic amine derivative according to claim 5, wherein each a' is 1, m is 3, n is 0, each $A_{2'}$ is a methyl group, each $R_{1'}$ group is a methyl group, each $R_{2'}$ is a hydrogen atom, and each $Ar_{5'}$ group is a phenyl group.

20. The aromatic amine derivative according to claim 5, wherein each a' is 1, m is 2, n is 1, and each $Ar_{5'}$ group is a phenyl group.

* * * * *